(12) United States Patent
Yu et al.

(10) Patent No.: US 9,180,223 B2
(45) Date of Patent: Nov. 10, 2015

(54) BIPHASIC OSTEOCHONDRAL SCAFFOLD FOR RECONSTRUCTION OF ARTICULAR CARTILAGE

(71) Applicant: THE TRUSTEES OF THE STEVENS INSTITUTE OF TECHNOLOGY, Hoboken, NJ (US)

(72) Inventors: Xiaojun Yu, Fishers, IN (US); Paul Lee, East Brunswick, NJ (US)

(73) Assignee: THE TRUSTEES OF THE STEVENS INSTITUTE OF TECHNOLOGY, Hoboken, NJ (US)

( * ) Notice: Subject to any disclaimer, the term of this patent is extended or adjusted under 35 U.S.C. 154(b) by 0 days.

(21) Appl. No.: 14/399,427

(22) PCT Filed: Mar. 14, 2013

(86) PCT No.: PCT/US2013/031634
§ 371 (c)(1),
(2) Date: Nov. 6, 2014

(87) PCT Pub. No.: WO2013/169374
PCT Pub. Date: Nov. 14, 2013

(65) Prior Publication Data
US 2015/0110846 A1  Apr. 23, 2015

Related U.S. Application Data

(60) Provisional application No. 61/645,319, filed on May 10, 2012.

(51) Int. Cl.
| | |
|---|---|
| *A61L 27/26* | (2006.01) |
| *A61F 2/28* | (2006.01) |
| *A61L 27/38* | (2006.01) |
| *A61L 27/54* | (2006.01) |
| *A61F 2/30* | (2006.01) |
| *C08L 5/08* | (2006.01) |
| *A61L 27/36* | (2006.01) |
| *B29C 53/56* | (2006.01) |

(52) U.S. Cl.
CPC . *A61L 27/26* (2013.01); *A61F 2/28* (2013.01); *A61F 2/30756* (2013.01); *A61L 27/365* (2013.01); *A61L 27/3852* (2013.01); *A61L 27/54* (2013.01); *B29C 53/562* (2013.01); *C08L 5/08* (2013.01); *A61F 2002/30016* (2013.01); *A61F 2002/3084* (2013.01); *A61F 2002/3092* (2013.01); *A61F 2002/30224* (2013.01); *A61F 2002/30293* (2013.01); *A61L 2430/02* (2013.01); *A61L 2430/06* (2013.01)

(58) Field of Classification Search
CPC ......... A61L 27/46; A61L 27/18; A61L 27/58; A61L 27/56; A61L 27/48; A61L 27/50; A61L 27/12; A61L 27/26; A61L 27/54; A61L 2430/02; A61L 27/32; A61L 27/44; A61L 31/148; A61L 2300/414; A61L 31/06
See application file for complete search history.

(56) References Cited

U.S. PATENT DOCUMENTS

| | | |
|---|---|---|
| 4,097,935 A | 7/1978 | Jarcho |
| 4,131,597 A | 12/1978 | Bluethgen et al. |
| 4,192,021 A | 3/1980 | Deibig et al. |
| 4,223,412 A | 9/1980 | Aoyagi et al. |
| 4,356,572 A | 11/1982 | Guillemin et al. |
| 4,629,464 A | 12/1986 | Takata et al. |
| 4,655,777 A | 4/1987 | Dunn et al. |
| 4,698,375 A | 10/1987 | Dorman et al. |
| 4,842,604 A | 6/1989 | Dorman et al. |
| 5,032,129 A | 7/1991 | Kurze et al. |
| 5,266,476 A | 11/1993 | Sussman et al. |
| 5,514,181 A | 5/1996 | Light et al. |
| 5,543,209 A | 8/1996 | Duquet et al. |
| 5,595,621 A | 1/1997 | Light et al. |
| 5,626,861 A | 5/1997 | Laurencin et al. |
| 5,629,009 A | 5/1997 | Laurencin et al. |
| 5,755,809 A | 5/1998 | Cohen et al. |
| 5,766,618 A | 6/1998 | Laurencin et al. |
| 5,866,155 A | 2/1999 | Laurencin et al. |
| 6,017,366 A | 1/2000 | Berman |
| 6,136,029 A | 10/2000 | Johnson et al. |
| 6,228,111 B1 | 5/2001 | Tormala et al. |
| 6,308,509 B1 | 10/2001 | Scardino et al. |
| 6,451,059 B1 | 9/2002 | Janas et al. |
| 6,689,166 B2 | 2/2004 | Laurencin et al. |

(Continued)

FOREIGN PATENT DOCUMENTS

WO   WO2005/089127 A2 *   9/2005   .............. A61L 27/26

OTHER PUBLICATIONS

Gilbert S, et al. Enhanced tissue integration during cartilage repair in vitro can be achieved by inhibiting chondrocyte death at the wound edge. Tissue Engineering Part A. 2009;15:1739-49.
Gotterbarm T, et al. An in vivo study of a growth-factor enhanced, cell free, two-layered collagen-tricalcium phosphate in deep osteochondral defects. Biomaterials. 2006;27:3387-95.
Grayson WL, et al., Engineering custom-designed osteochondral tissue grafts. Trends in biotechnology. 2008;26:181-9.
Griffith LG., Polymeric biomaterials. Acta Materialia. 2000;48:263-77.

(Continued)

*Primary Examiner* — Audrea Buckley
(74) *Attorney, Agent, or Firm* — Greenberg Traurig, LLP

(57) ABSTRACT

An osteochondral scaffold has a chondrogenic spiral scaffold in one end of an outer shell made of sintered microspheres, and an osteogenic spiral scaffold in the other end of the outer shell. Each spiral scaffold has nanofibers of a composition selected to promote attachment and proliferation of the desired types of cells. The nanofibers for the chondrogenic spiral scaffold have a different composition than the nanofibers for the osteogenic spiral scaffold. The nanofibers of each spiral scaffold are aligned to orient the attached cells so as to recreate the structure of the native tissue.

7 Claims, 9 Drawing Sheets

(56) References Cited

U.S. PATENT DOCUMENTS

| | | | |
|---|---|---|---|
| 6,906,044 | B2 | 6/2005 | Hermida Ochoa |
| 7,122,057 | B2 | 10/2006 | Beam et al. |
| 7,163,557 | B2 | 1/2007 | D'Eredita |
| 7,235,295 | B2 | 6/2007 | Laurencin et al. |
| 7,241,486 | B2 | 7/2007 | Pirhonen |
| 7,250,550 | B2 | 7/2007 | Overby et al. |
| 7,351,262 | B2 | 4/2008 | Bindseil et al. |
| 7,727,539 | B2 | 6/2010 | Laurencin et al. |
| 8,048,446 | B2 | 11/2011 | Lelkes et al. |
| 8,669,107 | B2 | 3/2014 | Detamore et al. |
| 8,906,362 | B2 | 12/2014 | Ferguson et al. |
| 2004/0191292 | A1 | 9/2004 | Chou |
| 2007/0083268 | A1 | 4/2007 | Teoh et al. |
| 2007/0269481 | A1 | 11/2007 | Li et al. |
| 2008/0220042 | A1 | 9/2008 | Hashi et al. |
| 2009/0028921 | A1 | 1/2009 | Arinzeh |
| 2010/0310623 | A1 | 12/2010 | Laurencin et al. |
| 2012/0088721 | A1 | 4/2012 | Shiedlin et al. |
| 2012/0093877 | A1 | 4/2012 | Zheng |
| 2012/0259415 | A1 | 10/2012 | Van Dyke et al. |
| 2012/0301507 | A1 | 11/2012 | Zheng |
| 2012/0308825 | A1 | 12/2012 | Ma et al. |

OTHER PUBLICATIONS

Griffon DJ, et al., Chitosan scaffolds: interconnective pore size and cartilage engineering. Acta biomaterialia. 2006;2:313-20.

Haleem AM, et al., Advances in tissue engineering techniques for articular cartilage repair. Operative Techniques in Orthopaedics. 2010;20:76-89.

Hegewald A, et al. Hyaluronic acid and autologous synovial fluid induce chondrogenic differentiation of equine mesenchymal stem cells: a preliminary study. Tissue and Cell. 2004;36:431-8.

Heilmann, F., et al., "Development of graded hydroxyapatite/CaC0(3) composite structures for bone ingrowth," Journal of Materials Science: Materials in Medicine, vol. 18 (Sep. 2007) pp. 1817-1824.

Ho STB, et al., An electrospun polycaprolactonecollagen membrane for the resurfacing of cartilage defects. Polymer International. 2010;59:808-17.

Ho STB, et al., The evaluation of a biphasic osteochondral implant coupled with an electrospun membrane in a large animal model. Tissue Engineering Part A. 2009;16:1123-41.

Holland TA, et al., Osteochondral repair in the rabbit model utilizing bilayered, degradable oligo (poly (ethylene glycol) fumarate) hydrogel scaffolds. Journal of Biomedical Materials Research Part A. 2005;75:156-67.

Hosseinkhani, K., et al., Bone regeneration through controlled release of bone morphogenetic protein-2 from 3-D tissue engineered nano-scaffold n Journal of Controlled Release, vol. 117 (2007), pp. 380-386.

Hung CT, et al., Anatomically shaped osteochondral constructs for articular cartilage repair. Journal of biomechanics. 2003;36:1853-64.

Hunziker EB. Articular cartilage repair: are the intrinsic biological constraints undermining this process insuperable? Osteoarthritis and cartilage. 1999;7:15-28.

Hunziker EB. Articular cartilage repair: basic science and clinical progress. A review of the current status and prospects. Osteoarthritis and cartilage. 2002;10:432-63.

Ikeda R, et al. The effect of porosity and mechanical property of a synthetic polymer scaffold on repair of osteochondral defects. International orthopaedics. 2009;33:821-8.

Im Gl,et al., A hyaluronate—atelocollagen/β-tricalcium phosphate—hydroxyapatite biphasic scaffold for the repair of osteochondral defects: A porcine study. Tissue Engineering Part A. 2010;16:1189-200.

Izquierdo R, et al. Biodegradable PCL scaffolds with an interconnected spherical pore network for tissue engineering. Journal of Biomedical Materials Research Part A. 2008;85A:25-35.

Jackson JK, et al., The characterization of paclitaxel-loaded microspheres manufactured from blends of poly (lactic-co-glycolic acid)(PLGA) and low molecular weight diblock copolymers. International journal of pharmaceutics. 2007;342:6-17.

Jiang J, et al., Bioactive stratified polymer ceramic-hydrogel scaffold for integrative osteochondral repair. Annals of Biomedical Engineering. 2010;38:2183-96.

Jiang T, et al., In vitro evaluation of chitosan/poly (lactic acid-glycolic acid) sintered microsphere scaffolds for bone tissue engineering. Biomaterials. 2006;27:4894-903.

Jones, J. R., et al., "Quantifying the 3D macrostructure of tissue scaffolds," Journal of Materials Science: Materials in Medicine, vol. 20 (2009), pp. 463-471.

Jordan JB. Comparison of Four Treatments for Patients with Severe Knee Cartilage Damage. 2001.

Kandel R, et al., In vitro formation of mineralized cartilagenous tissue by articular chondrocytes. In Vitro Cellular & Developmental Biology-Animal. 1997;33:174-81.

Karande, T. S., et al., "Diffusion in musculoskeletal tissue engineering scaffolds: design issues related to porosity, permeability, architecture, and nutrient mixing," Annual of Biomedical Engineering, vol. 32 (Dec. 2004), pp. 1728-1743.

Keeney M, et al., The osteochondral junction and its repair via biphasic tissue engineering scaffolds. Tissue Engineering Part B: Reviews. 2009;15:55-73.

Khan I, et al., Cartilage integration: evaluation of the reasons for failure of integration during cartilage repair. A review. Eur Cell Mater. 2008;16:26-39.

Khan, Y., et al., "Tissue engineering of bone: material and matrix considerations", Journal of Bone Joint Surgery America, vol. 90, Suppl. 1 (2008), pp. 36-42.

Kim B-S, et al. Growth and osteogenic differentiation of alveolar human bone marrow-derived mesenchymal stem cells on chitosan/hydroxyapatite composite fabric. Journal of Biomedical Materials Research Part A. 2012:n/a-n/a.

Kim IL, et al., Hydrogel design for cartilage tissue engineering: A case study with hyaluronic acid. Biomaterials. 2011.

Kim IY, et al. Chitosan and its derivatives for tissue engineering applications. Biotechnology Advances. 2008;26:1-21.

Kim TK, et al. Experimental Model for Cartilage Tissue Engineering to Regenerate the Zonal Organization of Articular Cartilage* 1. Osteoarthritis and cartilage. 2003;11:653-64.

Klein TJ, et al. Strategies for zonal cartilage repair using hydrogels. Macromolecular bioscience. 2009;9:1049-58.

Kofron, M.D., et al., "Novel tubular composite matrix for bone repair", Journal of Biomedical Materials Research Part A, Feb. 2007, pp. 415-425.

Kokubo, et al., "Solutions able to produce in vivo surface structure changes in bioactive glass-ceramic A-W," J. Biomed. Mater. Res., 24, 721-734 (1990).

Kong L., et al., "Preparation and Characterization of a Multilayer Biomimetic Scaffold for Bone Tissue Engineering", Journal of Biomaterials Applications, vol. 00 (2007), pp. 1-17.

Kreuz P, et al. Results after microfracture of full-thickness chondral defects in different compartments in the knee1. Osteoarthritis and cartilage. 2006;14:1119-25.

Laffargue, Ph., et al., "Evaluation of Human Recombinant Bone Morphogenetic Protein-2-Loaded Tricalcium Phosphate Implants in Rabbits' Bone Defects," Bone, vol. 25 (1999) No. 2, Supplement oo. 555-585.

Lam CXF,et al., Dynamics of in vitro polymer degradation of polycaprolactone-based scaffolds: accelerated versus simulated physiological conditions. Biomedical Materials. 2008;3:034108.

Lao L, et al., Chitosan modified poly(I-lactide) microspheres as cell microcarriers for cartilage tissue engineering. Colloids and Surfaces B: Biointerfaces. 2008;66:218-25.

Laurencin, C. T., et al., "A highly porous 3-dimensional polyphosphazene polymer matrix for skeletal tissue regeneration," Journal of Biomedical Materials Research, vol. 30 (1996) pp. 133-138.

Lee CT, et al., Biomimetic porous scaffolds made from poly (L-lactide)-g-chondroitin sulfate blend with poly (L-lactide) for cartilage tissue engineering. Biomacromolecules. 2006;7:2200-9.

(56) References Cited

OTHER PUBLICATIONS

Li Q, et al., Photocrosslinkable polysaccharides based on chondroitin sulfate. Journal of Biomedical Materials Research Part A. 2004;68:28-33.
Li X, et al., Coating electrospun poly (ε-caprolactone) fibers with gelatin and calcium phosphate and their use as biomimetic scaffolds for bone tissue engineering. Langmuir. 2008;24:14145-50.
Liao S, et al., Biomimetic electrospun nanofibers for tissue regeneration. Biomedical Materials. 2006;1:R45.
Lim S, et al., Preparation and evaluation of the in vitro drug release properties and mucoadhesion of novel microspheres of hyaluronic acid and chitosan. Journal of Controlled Release. 2000;66:281-92.
Loening AM, et al. Injurious mechanical compression of bovine articular cartilage induces chondrocyte apoptosis. Archives of biochemistry and biophysics. 2000;381:205-12.
Lu L, et al., Biodegradable polymer scaffolds for cartilage tissue engineering. Clinical Orthopaedics and Related Research. 2001;391:S251.
Luciani A, et al., PCL microspheres based functional scaffolds by bottom-up approach with predefined microstructural properties and release profiles. Biomaterials. 2008;29:4800-7.
Luciani A, et al., Solvent and melting induced microspheres sintering techniques: a comparative study of morphology and mechanical properties. Journal of Materials Science: Materials in Medicine. 2011:1-10.
Lyckfeldt, O., et al., "Processing of porous ceramics by 'starch consolidation'," Journal of the European Ceramics Society, vol. 18 (1998), pp. 131-140.
Mano J, et al., Osteochondral defects: present situation and tissue engineering approaches. Journal of Tissue Engineering and Regenerative Medicine. 2007;1:261-73.
Matsuda, N. et al., "Tissue Engineering Based on Cell Sheet Technology," Advanced Materials, vol. 19 (2007), pp. 3089-3099.
Mcintosh, L., et al., "Impact of bone geometry on effective properties of bone scaffolds," Acta Biomateriali, vol. 5 (2009), pp. 680-692.
MD KZ. Overview of Treatment Options for Articular Cartilage Repair: Past Present & Future. FDA; 2009.
Mercier NR, et al., Poly(lactide-co-glycolide) microspheres as a moldable scaffold for cartilage tissue engineering. Biomaterials. 2005;26:1945-52.
Mithoefer K, et al., Clinical efficacy of the microfracture technique for articular cartilage repair in the knee. The American Journal of Sports Medicine. 2009;37:2053.
Mithoefer K, et al. The microfracture technique for the treatment of articular cartilage lesions in the knee. J Bone Joint Surg Am. 2005;87:1911-20.
Moroni L, et al., 3D Fiber—Deposited Electrospun Integrated Scaffolds Enhance Cartilage Tissue Formation. Advanced Functional Materials. 2008;18:53-60.
Mrosek EH, et al. Porous tantalum and poly—ε—caprolactone biocomposites for osteochondral defect repair: Preliminary studies in rabbits. Journal of Orthopaedic Research. 2010;28:141-8.
Murugan R, et al., Design strategies of tissue engineering scaffolds with controlled fiber orientation. Tissue engineering. 2007;13:1845-66.
Niederauer G, et al. Evaluation of multiphase implants for repair of focal osteochondral defects in goats. Biomaterials. 2000;21:2561-74.
Nisbet D, et al., Review paper: a review of the cellular response on electrospun nanofibers for tissue engineering. Journal of Biomaterials Applications. 2009;24:7-29.
Nishimoto S, et al., Effect of chondroitin sulfate and hyaluronic acid on gene expression in a three-dimensional culture of chondrocytes. Journal of bioscience and bioengineering. 2005;100:123-6.
Nixon AJ, et al., Autologous chondrocyte implantation drives early chondrogenesis and organized repair in extensive full- and partial-thickness cartilage defects in an equine model. Journal of Orthopaedic Research. 2011;29:1121-30.
Oh SH, et al., in vitro and in vivo characteristics of PCL scaffolds with pore size gradient fabricated by a centrifugation method. Biomaterials. 2007;28:1664-71.

Okazaki R, et al. Sequential changes in transforming growth factor (TGF)-β1 concentration in synovial fluid and mRNA expression of TGF-β1 receptors in chondrocytes after immobilization of rabbit knees. Journal of bone and mineral metabolism. 2001;19:228-35.
O'Shea TM, et al., Bilayered scaffolds for osteochondral tissue engineering. Tissue Engineering Part B: Reviews. 2008;14:447-64.
"Pham, Q. P., et al., ""Eiectrospun Poly( E-caprolactone) Microfiber and Multilayer Nanofiber/Microfiber Scaffolds: Characterization of Scaffolds and Measurement of Cellular Infiltration""", Biomacromolecules, vol. 7 (2006), pp. 2796-2805."
Puppi D, et al., Polymeric materials for bone and cartilage repair. Progress in Polymer Science. 2010;35:403-40.
Ramires P, et al., The influence of titania/hydroxyapatite composite coatings on in vitro osteoblasts behaviour. Biomaterials. 2001;22:1467-74.
Redman S, et al., Current strategies for articular cartilage repair. Eur Cell Mater. 2005;9:23-32.
Ren, L., et al., "A novel strategy for prefabrication of large and axially vascularized tissue engineered bone by using an arteriovenous loop", Medical Hypotheses, vol. 71 (2008), pp. 737-740.
Rezwan, K., et al., "Biodegradable and bioactive porous polymer/inorganic composite scaffolds for bone tissue engineering", Biomaterials, vol. .27 (2006), pp. 3413-3431.
Sarasam A, et al., Characterization of chitosan- polycaprolactone blends for tissue engineering applications. Biomaterials. 2005;26:5500-8.
Schek RM, et al., Engineered osteochondral grafts using biphasic composite solid free-form fabricated scaffolds. Tissue engineering. 2004;10:1376-85.
Schmidmaier, G., et al., Biodegradable poly(D,L-lactide) coating of implants for continuous release of growth factors, Journal of Biomedical Materials Research, vol. 58 (2001), p. 449-455.
Sekiya I, et al., In vitro cartilage formation by human adult stem cells from bone marrow stroma defines the sequence of cellular and molecular events during chondrogenesis. Proceedings of the National Academy of Sciences. 2002;99:4397-402.
Sell S, et al. Extracellular matrix regenerated: tissue engineering via electrospun biomimetic nanofibers. Polymer International. 2007;56:1349-60.
Shah R, et al., Supramolecular design of self-assembling nanofibers for cartilage regeneration. Proceedings of the National Academy of Sciences. 2010;107:3293.
Shao HJ, et al., The phenotypic responses of human anterior cruciate ligament cells cultured on poly (• caprolactone) and chitosan. Journal of Biomedical Materials Research Part A. 2009;93:1297-305.
Shao HJ, et al., Modulation of gene expression and collagen production of anterior cruciate ligament cells through cell shape changes on polycaprolactone/chitosan blends. Biomaterials. 2010;31:4695-705.
Shao XX, et al., Evaluation of a hybrid scaffold/cell construct in repair of high-load-bearing osteochondral defects in rabbits. Biomaterials. 2006;27:1071-80.
Sharma B, et al. Designing zonal organization into tissue-engineered cartilage. Tissue engineering. 2007;13:405-14.
Shepherd D, et al., The'instantaneous' compressive modulus of human articular cartilage in joints of the lower limb. Rheumatology. 1999;38:124.
Shepherd DET, et al., Thickness of human articular cartilage in joints of the lower limb. Annals of the Rheumatic Diseases. 1999;58:27-34.
Sherwood JK, et al. A three-dimensional osteochondral composite scaffold for articular cartilage repair. Biomaterials. 2002;23:4739-51.
Shields KJ, et al., Mechanical properties and cellular proliferation of electrospun collagen type II. Tissue engineering. 2004;10:1510-7.
Shin HJ, et al. Electrospun PLGA nanofiber scaffolds for articular cartilage reconstruction: mechanical stability, degradation and cellular responses under mechanical stimulation in vitro. Journal of Biomaterials Science, Polymer Edition, 17. 2006;1:103-19.
Siebert C, et al., Healing of osteochondral transplants—animal experiment studies using a sheep model—Abstract, Zeitschrift fur Orthopadie and Ihre Grenzgebiete, 2001, 139(5):382-386.
Silva, M. M. C. G, et al., "The effect of anisotropic architecture on cell and tissue infiltration into tissue engineering scaffolds," Biomaterials, vol. 27 (2006) pp. 5909-5917.

(56) References Cited

OTHER PUBLICATIONS

Smith, L. A., et al., "Nano-fibrous scaffolds for tissue engineering", Colloids and Surfaces B: Biointerfaces, vol. 39 (2004 ), pp. 125-131.
Stammberger T, et al., Determination of 3D cartilage thickness data from MR imaging: computational method and reproducibility in the living. Magnetic resonance in medicine. 1999;41:529-36.
Steadman JR, et al., Outcomes of microfracture for traumatic chondral defects of the knee: average 11-year follow-up. Arthroscopy—the Journal of Arthroscopic and Related Surgery. 2003;19:477-84.
Stephens—Altus J, et al., Development of bioactive photocrosslinkable fibrous hydrogels. Journal of Biomedical Materials Research Part A. 2011.
Strauss E, et al., The efficacy of intra-articular hyaluronan injection after the microfracture technique for the treatment of articular cartilage lesions. The American Journal of Sports Medicine. 2009;37:720.
Sun H, et al., The in vivo degradation, absorption and excretion of PCL-based implant. Biomaterials. 2006;27:1735-40.
Sun, J. S., et.al., "The effects of calcium phosphate particles on the growth of osteoblasts," Journal of Biomedical Materials Research, vol. 4 (1996) pp. 324-335.
Tamai N, et al. A new biotechnology for articular cartilage repair: subchondral implantation of a composite of interconnected porous hydroxyapatite, synthetic polymer (PLA-PEG), and bone morphogenetic protein-2 (rhBMP-2). Osteoarthritis and cartilage. 2005;13:405-17.
Tang, Z., et al., "Biomedical Applications of Layer-by-Layer Assembly: From Biomimetics to Tissue Engineering", Advanced Materials, vol. 18 (2006), pp. 3203-3224.
Teng S.H., et al., "Collagen/hydroxyapatite composite nanofibers by electrospinning", Materials Letters, vol. 62 (2008), pp. 3055-3058.
Thorvaldsson A, et al., Electrospinning of highly porous scaffolds for cartilage regeneration. Biomacromolecules. 2008;9:1044-9.
Thuaksuban N, et al., Biodegradable polycaprolactone-chitosan three-dimensional scaffolds fabricated by melt stretching and multilayer deposition for bone tissue engineering: assessment of the physical properties and cellular response. Biomedical Materials. 2011;6:015009.
Valmikinathan CM, et al., Novel nanofibrous spiral scaffolds for neural tissue engineering. Journal of neural engineering. 2008;5:422.
Varghese S, et al., Chondroitin sulfate based niches for chondrogenic differentiation of mesenchymal stem cells. Matrix biology. 2008;27:12-21.
Venugopal, J., et al., "Mineralization of osteoblasts with electrospun collagen/hydroxyapatite nanofibers", Journal of Materials Science: Materials in Medicine, vol. 19 (2008), pp. 2039-2046.
Wang, J, et al., Spiral—structured, nanofibrous, 3D scaffolds for bone tissue engineering. Journal of Biomedical Materials Research Part A. 2010;93:753-62.
Wang, J., et al., "Enhanced osteoblast response to 3D spiral nanofibrous scaffolds in rotating wall vessel (RWV) bioreactors," Annual Conference of Orthopedics Research Society (ORS), Las Vegas, NV, Feb. 2009.
Wang, J., et al., "Spiral-structured nanofibrous, 3D scaffolds for bone tissue engineering", (presentation slides) Annual Conference of Society for Biomaterials, Chicago, Apr. 2007.
Wise JK, et al., Chondrogenic differentiation of human mesenchymal stem cells on oriented nanofibrous scaffolds: engineering the superficial zone of articular cartilage. Tissue Engineering Part A. 2008;15:913-21.
Woo, K. M., et al., "Nano-fibrous scaffolding promotes osteoblast differentiation and biomineralization", Biomaterials, vol. 28 (2007), pp. 335-343.
Woodfield T, et al., Polymer scaffolds fabricated with pore-size gradients as a model for studying the zonal organization within tissue-engineered cartilage constructs. Tissue engineering. 2005;11:1297-311.
Xiao X, et al., Preparation and characterization of hydroxyapatite/polycaprolactone—chitosan composites. Journal of Materials Science: Materials in Medicine. 2009;20:2375-83.

Xue D, et al. Osteochondral repair using porous poly (lactide—co—glycolide)/nano—hydroxyapatite hybrid scaffolds with undifferentiated mesenchymal stem cells in a rat model. Journal of Biomedical Materials Research Part A. 2010;94:259-70.
Yamane S, et al. Effect of pore size on in vitro cartilage formation using chitosan based hyaluronic acid hybrid polymer fibers. Journal of Biomedical Materials Research Part A. 2007;81:586-93.
Yan J, et al., Potential use of collagen-chitosan-hyaluronan tri-copolymer scaffold for cartilage tissue engineering. Artificial Cells, Blood Substitutes and Biotechnology. 2006;34:27-39.
Yang F, et al., Biomimetic calcium phosphate coating on electrospun poly (•-caprolactone) scaffolds for bone tissue engineering. Chemical Engineering Journal. 2008;137:154-61.
Yang, J., et. al., "Cell delivery in regenerative medicine: The cell sheet engineering approach," Journal of Controlled Release, vol. 116 (2006), pp. 193-203.
Yang, J., et. al., "Reconstruction of functional tissues with cell sheet engineering," Biomaterials, vol. 28 (2007), pp. 5033-5043.
Yasuda K, et al. A Novel Double—Network Hydrogel Induces Spontaneous Articular Cartilage Regeneration in vivo in a Large Osteochondral Defect. Macromolecular bioscience. 2009;9:307-16.
Yasuda, H. Y., et.al., "Preparation of hydroxyapatite/ ex:.—tricalcium phosphate composites by colloidal process," Science and Technology of Adv. Materials, vol. 3 (2002), pp. 29-33.
Yu H, et al., Composition of cartilagenous tissue with mineralized and non-mineralized zones formed in vitro. Biomaterials. 1997;18:1425-31.
Yu, H., et al., "Improved tissue-engineered bone regeneration by endothelial cell mediated vascularization", Biomaterials, vol. 30 (2009), pp. 508-517.
Yunos D, et al., Stratified scaffolds for osteochondral tissue engineering applications: Electrospun PDLLA nanofibre coated Bioglass®-derived foams. Journal of Biomaterials Applications. 2011.
Zhang L, et al. Preparation of collagen-chondroitin sulfate-hyaluronic acid hybrid hydrogel scaffolds and cell compatibility in vitro. Carbohydrate Polymers. 2010.
Zhang Y, et al., Characterization of the surface biocompatibility of the electrospun PCL-collagen nanofibers using fibroblasts. Biomacromolecules. 2005;6:2583-9.
Zhu B, et al., Alignment of osteoblast-like cells and cell-produced collagen matrix induced by nanogrooves. Tissue engineering. 2005;11:825-34.
Zizak I, et al. Characteristics of mineral particles in the human bone/cartilage interface. Journal of Structural Biology. 2003;141:208-17.
Zolnik BS, et al., Evaluation of in vivo in vitro release of dexamethasone from PLGA microspheres. Journal of Controlled Release. 2008;127:137-45.
Ahn JH, Lee TH, Oh JS, Kim SY, Kim HJ, Park IK, et al. A Novel Hyaluronate—Atelocollagen/β-TCP—Hydroxyapatite Biphasic Scaffold for the Repair of Osteochondral Defects in Rabbits. Tissue Engineering Part A. 2009;15:2595-604.
Anil Kumar, P. R., et al., "Alternate method for grafting thermoresponsive polymer for transferring in vitro cell sheet structures," Journal of Applied Polymer Science, vol. 105 (2007), pp. 2245-2251.
Anil Kumar, P. R., et al., "Rapid and complete cellularization of hydroxyapatite for bone tissue engineering", Acta Biomaterialia, vol. 1 (2005), pp. 545-552.
Bal BS, Rahaman MN, Jayabalan P, Kuroki K, Cockrell MK, Yao JQ, et al. In vivo outcomes of tissue—engineered osteochondral grafts. Journal of Biomedical Materials Research Part B: Applied Biomaterials. 2010;93:164-74.
Barnes, C. P., et al., "Nanofiber technology: Designing the next generation of tissue engineering scaffolds," Advanced Drug Delivery Reviews, vol. 59 (2007), pp. 1413-1433.
Beş kardeş IG, Gümüş derelioğlu M. Biomimetic apatite-coated PCL scaffolds: effect of surface nanotopography on cellular functions. Journal of bioactive and compatible polymers. 2009;24:507-24.
Bhosale AM, Richardson JB. Articular cartilage: structure, injuries and review of management. British medical bulletin. 2008;87:77-95.

(56) References Cited

OTHER PUBLICATIONS

BioMedGPS' SmartTRAK OrthoBio Database Projects US Cartilage Replacement Market Will Reach $58 Million by 2014. In: BioMedGPS, editor.: BioMedGPS, LLC; 2010.
Boonsongrit, Y., "Controlled Release of bovine serum albumin from hydroxyapatite microspheres for protein delivery system," Materials Science and Engineering B, vol. 148 (2008) pp. 162-165.
Borden M, Attawia M, Laurencin CT. The sintered microsphere matrix for bone tissue engineering: in vitro osteoconductivity studies. Journal of biomedical materials research. 2002;61:421-9.
Borden, M., et al., "Structural and human cellular assessment of a novel microsphere-based tissue engineered scaffold for bone repair," Biomaterials, vol. 24 (Feb. 2003), pp. 597-609.
Borden, M., et al., "Tissue engineered microsphere-based matrices for bone repair: design and evaluation", Biomaterials, vol. 23 (2002), pp. 551-559.
Boyan, B. D., et al., "Mechanisms involved in osteoblast response to implant surface morphology," Annual Review of Materials Research, vol. 31 (2001), pp. 357-371.
Boyan, B. D., et al., "Role of material surfaces in regulating bone and cartilage cell response," Biomaterials, vol. 17 (1996), pp. 137-146.
Brehm W, et al. Repair of superficial osteochondral defects with an autologous scaffold-free cartilage construct in a caprine model: implantation method and short-term results. Osteoarthritis and cartilage. 2006;14:1214-26.
Bryant SJ, et al., Synthesis and characterization of photopolymerized multifunctional hydrogels: water-soluble poly (vinyl alcohol) and chondroitin sulfate macromers for chondrocyte encapsulation. Macromolecules. 2004;37:6726-33.
Burgin LV, et al., Impact testing to determine the mechanical properties of articular cartilage in isolation and on bone. Journal of Materials Science: Materials in Medicine. 2008;19:703-11.
Burkhardt D, et al., A novel microassay for the quantitation of the sulfated glycosaminoglycan content of histological sections: its application to determine the effects of Diacerhein on cartilage in an ovine model of osteoarthritis. Osteoarthritis and cartilage. 2001;9:238-47.
Cai K., et al., "Surface modification of titanium thin film with chitosan via electrostatic selfassembly technique and its influence on osteoblast growth behavior", Science: Materials in Medicine, vol. 19 (2008), pp. 499-506.
Capito RM, et al., Scaffold-based articular cartilage repair. Engineering in Medicine and Biology Magazine, IEEE. 2003;22:42-50.
Carmont MR, et al., Delayed incorporation of a TruFit plug: perseverance is recommended. Arthroscopy: The Journal of Arthroscopic & Related Surgery. 2009;25:810-4.
Chang CH, et al., Gelatin-chondroitin-hyaluronan tri-copolymer scaffold for cartilage tissue engineering. Biomaterials. 2003;24:4853-8.
Chang KY, et al., Fabrication and characterization of poly (γ-glutamic acid)-graft-chondroitin sulfate/polycaprolactone porous scaffolds for cartilage tissue engineering. Acta biomaterialia. 2009;5:1937-47.
Chang KY, et al., The application of type II collagen and chondroitin sulfate grafted PCL porous scaffold in cartilage tissue engineering. Journal of Biomedical Materials Research Part A. 2010;92:712-23.
Chesnutt BM, et al., Composite chitosan/nano-hydroxyapatite scaffolds induce osteocalcin production by osteoblasts in vitro and support bone formation in vivo. Tissue Engineering Part A. 2009;15:2571-9.
Choi SH, et al., Synthesis and characterization of elastic PLGA/PCL/PLGA tri-block copolymers. Journal of Biomaterials Science, Polymer Edition. 2002;13:1163-73.
Chuenjitkuntaworn B, et al., Polycaprolactone/hydroxyapatite composite scaffolds: Preparation, characterization, and in vitro and in vivo biological responses of human primary bone cells. Journal of Biomedical Materials Research Part A. 2010;94:241-51.

Chung C, et al., Influence of three-dimensional hyaluronic acid microenvironments on mesenchymal stem cell chondrogenesis. Tissue Engineering Part A. 2008;15:243-54.
Ciapetti G, et al., Osteoblast growth and function in porous polycaprolactone matrices for bone repair: a preliminary study. Biomaterials. 2003;24:3815-24.
Clarke IC., Articular cartilage: a review and scanning electron microscope study: 1. The interterritorial fibrillar architecture. Journal of Bone and Joint Surgery-British Volume. 1971;53:732.
Clegg DO, et al. Glucosamine, chondroitin sulfate, and the two in combination for painful knee osteoarthritis. New England Journal of Medicine. 2006;354:795-808.
Correia CR, et al. Chitosan Scaffolds Containing Hyaluronic Acid for Cartilage Tissue Engineering. Tissue Engineering Part C: Methods. 2011;17:717-30.
Descamps, M. et al, "Manufacture of macroporous 13-tricalcium phosphate bioceramics," ScienceDirect, (2008) pp. 147-157.
Donnelly E, et al., Primary cilia are highly oriented with respect to collagen direction and long axis of extensor tendon. Journal of Orthopaedic Research. 2010;28:77-82.
Dorotka R, et al., Repair of articular cartilage defects treated by microfracture and a three-dimensional collagen matrix. Biomaterials. 2005;26:3617-29.
Eltawil N, et al., A novel in vivo murine model of cartilage regeneration. Age and strain-dependent outcome after joint surface injury. Osteoarthritis and cartilage. 2009;17:695-704.
Erggelet C, et al. Formation of cartilage repair tissue in articular cartilage defects pretreated with microfracture and covered with cell—free polymer—based implants. Journal of Orthopaedic Research. 2009;27:1353-60.
Erisken, C., et al., "Functionally graded electrospun polycaprolactone and ~-tricalcium phosphate nanocomposites for tissue engineering applications," Biomaterials, vol. 29 (2008), pp. 4065-4073.
Eyre D. Collagen of articular cartilage. Arthritis research. 2002;4:30-5.
Fan H, et al., Porous gelatin-chondroitin-hyaluronate tri copolymer scaffold containing microspheres loaded with TGF 1 induces differentiation of mesenchymal stem cells in vivo for enhancing cartilage repair. Journal of Biomedical Materials Research Part A. 2006;77:785-94.
Fan H, et al. Cartilage regeneration using mesenchymal stem cells and a PLGA-gelatin/chondroitin/hyaluronate hybrid scaffold. Biomaterials. 2006;27:4573-80.
Farndale R, et al., Improved quantitation and discrimination of sulphated glycosaminoglycans by use of dimethylmethylene blue. Biochimica et Biophysica Acta (BBA)-General Subjects. 1986;883:173-7.
Frenkel S, et al. Regeneration of articular cartilage-Evaluation of osteochondral defect repair in the rabbit using multiphasic implants. Osteoarthritis and cartilage. 2005;13:798-807.
Frenkel SR, et al., Scaffolds for Articular Cartilage Repair. Annals of Biomedical Engineering. 2004;32:26-34.
Fujihara, K., et al., "Guided bone regeneration membrane made of polycaprolactone calcium carbonate composite nanofibers," Biomaterials, vol. 26 (2005), pp. 4139-4147.
Garcia-Giralt N, et al. A porous PCL scaffold promotes the human chondrocytes redifferentiation and hyaline-specific extracellular matrix protein synthesis. Journal of Biomedical Materials Research Part A. 2008;85A:1082-9.
Gauthier, O. et al., "Kinetic study of bone ingrowth and ceramic resorption associated with the implantation of different injectable calcium-phosphate bone substitutes," Journal of Biomedical Materials Research, vol. 47 (1999), pp. 28-35.
Getgood A, et al. Evaluation of early-stage osteochondral defect repair using a biphasic scaffold based on a collagen-glycosaminoglycan biopolymer in a caprine model. The Knee. 2011.
Gilbert S, et al., Inhibition of chondrocyte death at the wound edge enhances integrative cartilage repair. European Cells and Materials. 2008;16:39.

* cited by examiner

BIPHASIC OSTEOCHONDRAL SCAFFOLD FOR RECONSTRUCTION OF ARTICULAR CARTILAGE

CROSS-REFERENCE TO RELATED APPLICATIONS

The present application claims the benefit of U.S. Provisional Patent Application No. 61/645,319, filed on May 10, 2012, which is incorporated herein by reference.

STATEMENT REGARDING FEDERALLY SPONSORED RESEARCH

Not applicable.

FIELD OF THE INVENTION OR TECHNICAL FIELD

The present invention is directed to a synthetic osteochondral scaffold for promoting articular cartilage regeneration.

BACKGROUND OF THE INVENTION

Articular cartilage covers the end of all diarthroidal joints, allowing the bones to slide against each other without actually coming into contact with each other. Due to the lack of vascularity above the subchondral region, healing of damaged cartilage is very rare. Thus, the body generally cannot heal the articular cartilage on its own and the eventual degradation of the tissue leads to painful osteoarthritis and limited movement.

Current treatments for osteoarthritis include joint replacement, microfracturing to release mesenchymal stem cells, autograft procedures such as mosaicplasty or osteochondral autografts that require a donor site and additionally surgery, autologous chondrocyte implantation under the periosteal flap, and scaffold implantation. Unfortunately, although there are numerous treatments, none have been marked as a gold standard due to each one having its own drawbacks, especially when it comes to reproducing the exact physiological structure of articular cartilage capable of integrating with the surrounding tissue and bone.

Though the thickness of the articular cartilage covering the surface of a joint is at most 3 mm, cartilage itself has a fairly complex structure. The cartilage includes living cells (e.g., chondrocytes) and extracellular material (ECM) such as collagen, glycosaminoglycans (GAGs), and proteoglycans. The upper (superficial) zone of the cartilage layer has a higher concentration of collagen and lower concentration of GAGs attached to proteoglycans, thus providing it with the highest density of cells (e.g., chondrocytes) within the cartilage layer, as well as the highest water content. Cells are oriented in a ellipsoidal shape parallel to the subchondral surface (i.e., the surface of the underlying bone that supports the cartilage) where the collagen fibrils and proteoglycans are also arranged parallel to each other, providing strong shear resistance and lubrication. The transitional zone, which is between the superficial zone and middle (radial) zone, has a lower cell density and larger collagen nanofibers oriented in a random fashion. Lastly, the radial zone has cells that are oriented in a perpendicular fashion to the subchondral surface, and has the largest-diameter collagen fibrils with the highest concentration of proteoglycans and the lowest cell density of the three zones. The greater amount of proteoglycan and orientation of the collagen fibrils along with the cellular orientation provides compressive strength and a medium for transferring compressive load to the subchondral bone.

Damage to the cartilage layer may also involve damage to the underlying subchondral bone. Bone tissue includes progenitor cells that may be recruited to regenerate both bone and cartilage. However, critical defects are not able to be healed by the bone's natural regenerative processes. When this occurs, there is a need for a bone graft or substitute to aid in the healing. Autografts are generally considered to be the gold standard in most tissue engineering applications due to their excellent compatibility with the host, and their osteoconductivity, osteoinductivity, and osteogenicity. But the use of autografts is plagued by supply issues and donor site morbidity issues. Allografts, despite being osteoconductive and fairly abundant in supply, can be associated with disease transmissions and require processing, preservation, and sterilization steps that decrease the healing properties of the allograft. Synthetic materials, although they are usually only osteoconductive, are readily available and easy to modify in terms of structure, mechanical strength, topology, and efficacy. Further, the regenerated bone and cartilage must be integrated to prevent delamination due to the transfer of kinetic energy from the cartilage to the bone as the joint is moved.

When there is a partial depth defect (i.e., the defect does not penetrate through the cartilage layer), progenitor cells from the bone marrow cannot be recruited to form new cartilage, thus repair will be extremely limited without the bone marrow mesenchymal cells. But when there is a full thickness defect (i.e., an osteochondral defect), even though the mesenchymal stem cells are released, there is no structure on which the cells can attach, proliferate, and differentiate. In such a situation, the stem cells become fibrocartilage, which is a poor substitute for articular cartilage due to its lack of mechanical strength and lubrication properties. Thus, a bone scaffold should be included as part of the osteochondral graft for full integration of the hyaline cartilage. Through the use of osteochondral grafts, the cartilage graft can be anchored securely to the substrate below through regeneration of the bone. Synthetic osteochondral implants may also be used to promote simultaneous integration of the bone and cartilage tissue at the implant site.

SUMMARY OF THE INVENTION

The present invention includes, among other things, an osteochondral scaffold for regeneration of cartilage and the adjoining bone, and a method of making same. The osteochondral scaffold includes a cylindrical outer shell including a plurality of microspheres sintered together as a unitary structure having a first hollow end and a second hollow end opposite said first hollow end. The osteochondral scaffold also includes a first spiral scaffold (a chondrogenic scaffold) having a plurality of nanofibers substantially aligned with each other. The nanofibers of the first spiral scaffold include components, such as the glycosaminoglycans chondroitin sulfate and hyaluronic acid to promote attachment, proliferation, and differentiation of mesenchymal stem cells into chondrocytes. Further, the osteochondral scaffold also includes a second spiral scaffold (an osteogenic scaffold) having a plurality of nanofibers substantially aligned with each other. The nanofibers of the second spiral scaffold include components, such as hydroxyapatite, β-glycerophosphate, and/or β-tricalcium phosphate (βTCP) to promote attachment, proliferation and differentiation of mesenchymal stem cells into osteoblasts, but in different proportions than in the first spiral scaffold. The first spiral scaffold resides in the first hollow end of the outer shell, and the second spiral scaffold resides in the second hollow end of the outer shell.

BRIEF DESCRIPTION OF FIGURES

For a more complete understanding of the present invention, reference is made to the following detailed description of an exemplary embodiment considered in conjunction with the accompanying drawings, in which.

DETAILED DESCRIPTION OF THE INVENTION

Osteochondral scaffolds made according to embodiments of the present invention can be used to facilitate the simultaneous regeneration of bone and cartilage and the integration of these tissues at the implant site. The regenerated cartilage has a zonal structure similar to that of native cartilage. Reconstructing the cartilage simultaneously with the subchondral bone addresses the issue of delamination (i.e., separation of the cartilage from the bone. Through the use of such osteochondral scaffolds, bone and cartilage may more successfully bond to each other than they would through the use of a cartilage scaffold alone.

Osteochondral scaffolds are typically cylindrical in geometry and are inserted into a matching defect site formed by removing a cylinder of tissue around the defect, cutting through the cartilage and into the underlying bone.

Figure 1:
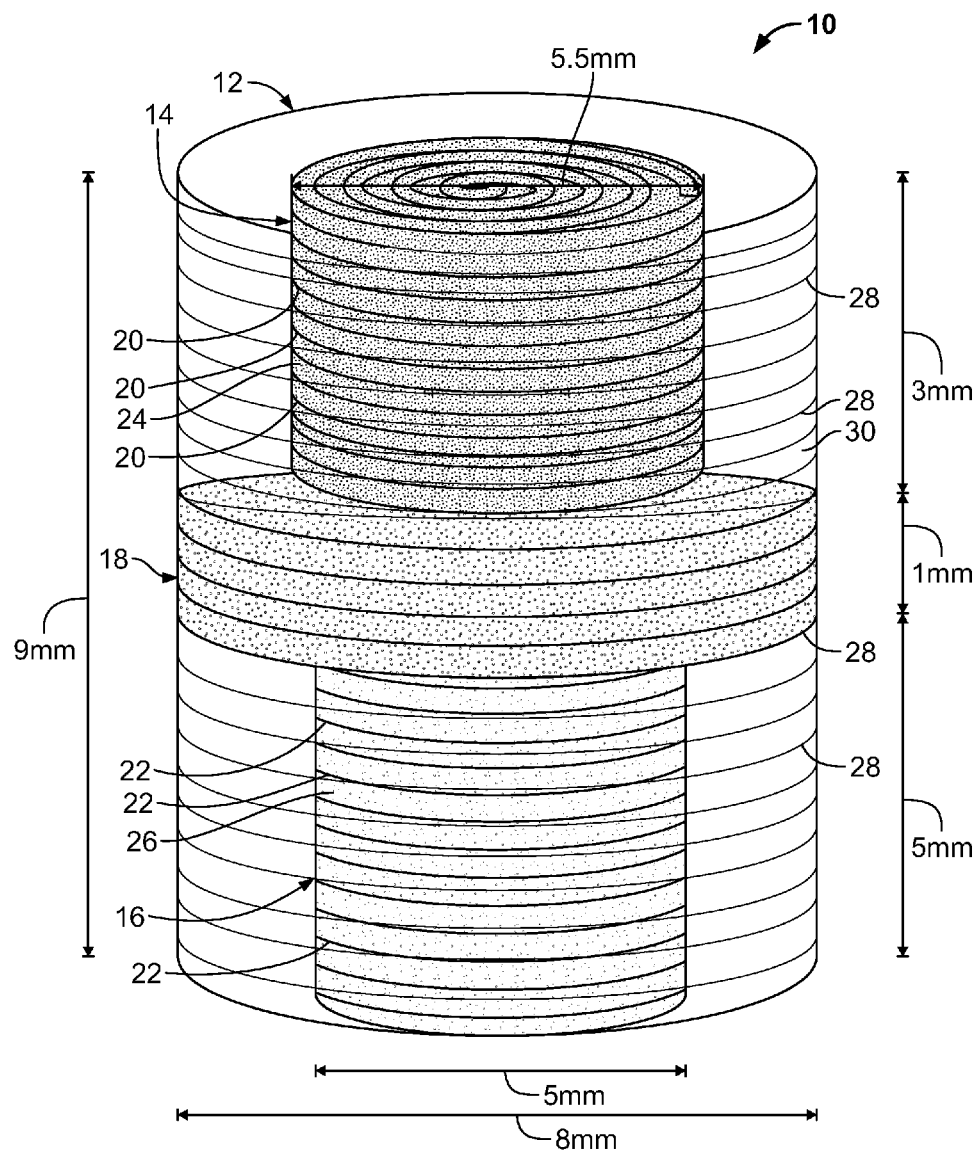
FIG. 1 is a schematic diagram of an osteochondral scaffold according to an embodiment of the present invention.

FIG. 1 is a schematic diagram of an osteochondral scaffold 10 according to an embodiment of the present invention, while FIGS. 2A, 2B, 3A-3D, and 4 are photographs of an osteochondral scaffold according several related embodiments of the present invention. FIGS. 1-4 may be referred to together for the purpose of the following discussion.

Turning first to FIG. 1, an osteochondral scaffold 10 according to an embodiment of the present invention comprises an outer shell 12 of sintered microspheres for providing structural strength to the scaffold 10, an upper spiral scaffold 14 for regenerating cartilage; and a lower spiral scaffold 16 for regenerating bone. The upper spiral scaffold 14, in all of its embodiments, is also referred to herein as a "cartilage regenerating scaffold," and the lower spiral scaffold 16, in all of its embodiments, is also referred to herein as a "bone-regenerating scaffold." The upper and lower scaffolds 14, 16 reside within the outer shell 12, and may be separated by a separator layer 18 of sintered microspheres, which itself may be bonded with the outer shell 12. The upper and lower scaffolds 14, 16 may be made of soft materials, and may require support from the outer shell 12.

For the upper areas of the outer shell, the microspheres may have diameters of 100-500 μm, and any range in between. Microspheres in the range of about 400-500 μm are particularly useful for attachment and migration of chondroctytes and their precursor cells. The microspheres in the middle area of the outer shell, which may include a separator layer, have diameters of less than 500 μm to stimulate the growth of mineralized cartilage. The microspheres in the lower area of the outer shell, which is intended to stimulate regrowth of bone, have diameters in the range of about 100-500 μm, and any range in between. Microspheres in the range of about 300-400 μm are particularly useful for increased osteoblast attachment and proliferation, and their differentiation from mesenchymal stem cells.

In some embodiments of the present invention, the upper and lower scaffolds 14, 16 have electrospun nanofibers 20, 22 on their surfaces, such as surfaces 24, 26, to promote cell growth and adhesion. Similarly, in some embodiments of the present invention, the outer shell 12 may have electrospun nanofibers 28 on its outer surface 30. Nanofibers 20, 22, 28 are shown in FIG. 1 in a horizontal orientation. Nanofibers having a vertical orientation may also be used, as well as overlapping vertical and horizontal nanofibers. Such electrospun nanofibers are discussed more fully elsewhere herein.

In embodiments of the present invention, the osteochondral scaffold has a length sufficient to extend throughout an osteochondral defect, from within the bone to the outer surface of the adjacent cartilage. In the embodiment of FIG. 1, the outer shell 14 has a length of about 9 mm and an outer diameter of about 8 mm. The upper scaffold 12 has a length of about 3 mm (or a length similar to the thickness of the cartilage layer to be regenerated) and an outer diameter of about 5.5 mm. The lower scaffold 16 has a length of about 5 mm and an outer diameter of about 5 mm. The separator layer 18 has a length of about 1 mm and an outer diameter of about 10 mm. The aforesaid dimensions are approximate and may be varied according to the dimensions of the osteochondral defect.

Figure 2A:
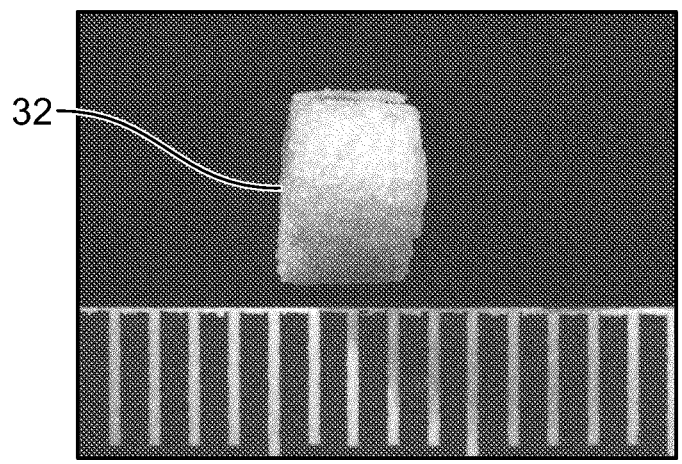
FIG. 2A is a photograph of a side view of a spiral scaffold according to an embodiment of the present invention.
Figure 2B:
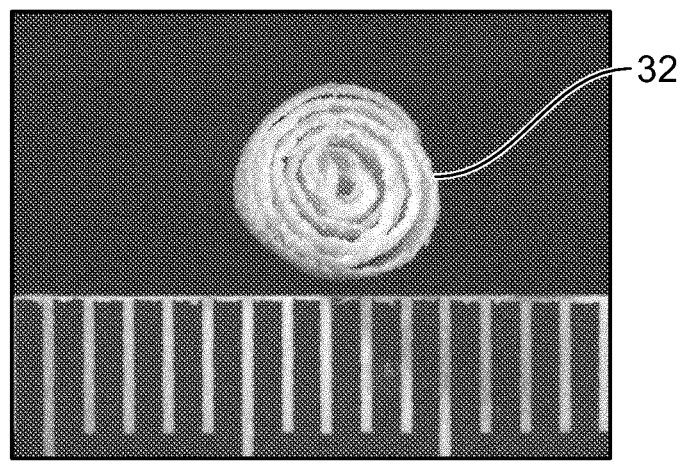
FIG. 2B is a photograph of a top view of the spiral scaffold of FIG. 2A.
Figure 3A:
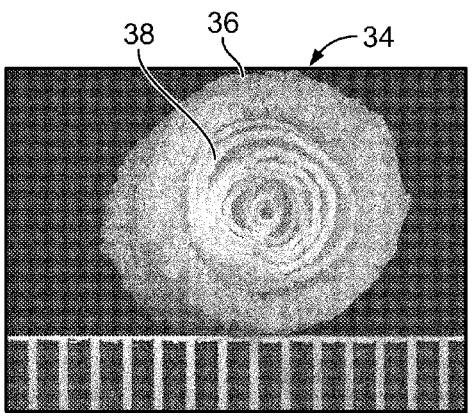
FIG. 3A is a photograph of a top view of a partially completed osteochondral scaffold according to an embodiment of the present invention.
Figure 3B:
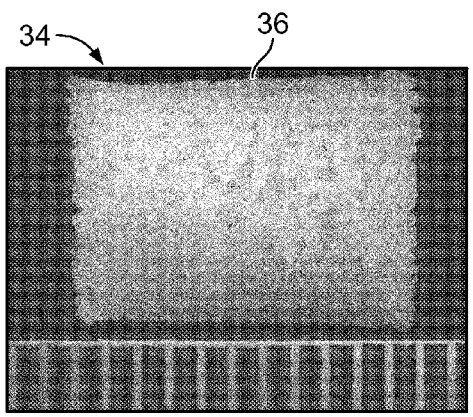
FIG. 3B is a photograph of a side view of the osteochondral scaffold of FIG. 3A.
Figure 3C:
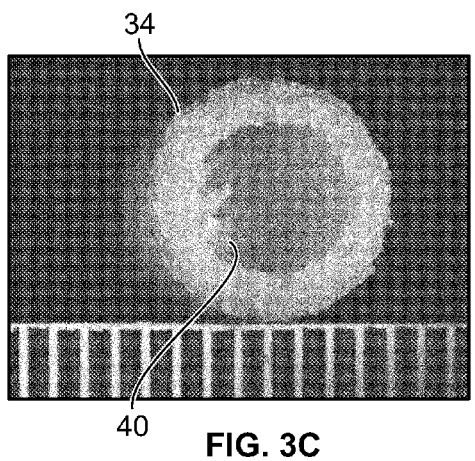
FIG. 3C is a photograph of a bottom view of the osteochondral scaffold of FIG. 3A.
Figure 3D:
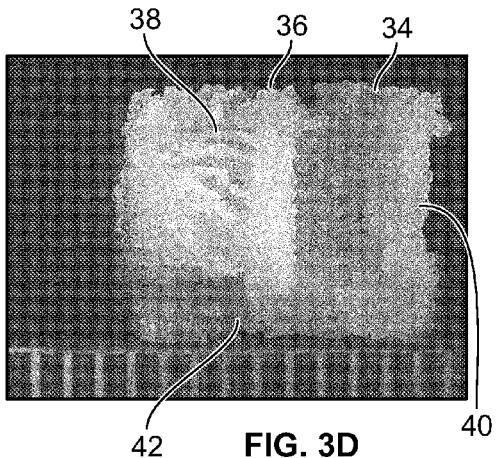
FIG. 3D is a photograph of a lengthwise cross-section of the osteochondral scaffold of FIG. 3A.
Figure 4:
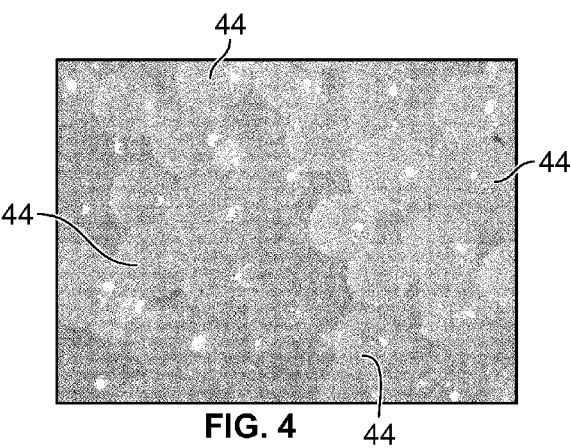
FIG. 4 is an enlarged photograph of a portion of the outer shell of the osteochondral scaffold of FIG. 3A.

Referring to other embodiments of the osteochondral scaffold, FIGS. 2A and 2B are photographs (side view and top view, respectively) of an embodiment of a spiral scaffold 32 that is similar to the spiral scaffolds 14, 16 of osteochondral scaffold 10 of FIG. 1. FIGS. 3A-3D are photographs of an osteochondral scaffold 34, of a type similar to osteochondral scaffold 10 of FIG. 1. FIG. 3A is a top view of osteochondral scaffold 34 showing an outer shell 36 of sintered microspheres and a spiral scaffold 38 residing within the outer shell 36. FIG. 3B is a side view of the osteochondral scaffold 34, showing the outer shell 36. Although not visible in FIG. 3B, nanofibers have been spun onto the left-hand portion of the outer shell 34. FIG. 3C is a bottom view of osteochondral scaffold 34 showing a chamber 40 into which a second spiral scaffold (not shown) would be inserted. FIG. 3D is a photograph of a lengthwise cross-section of osteochondral scaffold 34, showing the outer shell 36, the spiral scaffold 38, the chamber 40, and a separator layer 42. FIG. 4 is an enlargement of an outer shell, similar to outer shells 12, 36, showing sintered microspheres 44. The scales shown in FIGS. 2A, 2B, and 3A-3D are demarcated in millimeters (mm).

The components of the osteochondral scaffolds 10, 34 may be made of biocompatible, biodegradable materials, such that the implanted scaffolds 10, 34 are consumed to allow ingrowth of bone and/or cartilage tissue. Suitable materials include polycaprolactone (PCL), alone or in combination with poly (lactic glycolic) acid (PLGA). Other suitable materials include poly lactic acid, poly glycolic acid, polyurethane, chitosan, alginate, and gelatin. Other materials, such as chondroitin sulfate (CS), hyaluronan (HA), chitosan, collagen II, β-glycerophosphate, hydroxyapatite, bone morphogenetic protein, dexamethazone or a caspase inhibitor (e.g., Z-VAD-FMK ("ZVF")), may be used to promote cell growth and adhesion to the osteochondral scaffold, or otherwise aid in regenerating bone and cartilage. Other suitable materials for this purpose include poly lactic acid, poly glycolic acid, polyurethane, chitosan, alginate, and gelatin.

Expanding on the discussion of materials presented above, there are numerous substances which may be incorporated into the outer shell 12, spiral scaffolds 14, 16, or nanofibers 20, 22, 28 to aid in cell attachment, growth, and differentiation. A caspase inhibitor (e.g., ZVF) can be integrated into the electrospun nanofibers to increase lateral integration of the cartilage. The addition of a caspase inhibitor, which minimizes cellular apoptosis, also minimizes the zone of death upon debridement and implantation of the scaffold at the wound site. Thus, providing a caspase inhibitor should allow a more uniform articular cartilage to form.

The issue of the eventual separation of regenerated cartilage from the underlying bone can be addressed through the use of hydroxyapatite or other substances to promote the formation of a zone of mineralized cartilage. In the natural environment, the presence of mineralized cartilage between bone and cartilage mediates the differences in elastic modulus between the two tissues. This layer of mineralized cartilage helps to transmit compressive forces down to the bone without fracturing the cartilage. A suitable layer of mineralized cartilage can be induced to form by including a thin apatite-coated PCL sheet, or a layer of microspheres embedded with β-glycerophosphate and ascorbic acid, in the osteochondral scaffold near the position where a natural layer of mineralized cartilage would be expected to form. For example, the microspheres may be incorporated in the separator layer 18.

PLGA and PCL are both biodegradable and biocompatible polymers that have been used in many different types of scaffolds. They can bind drugs for timed release of therapeutic agents, which is practical for use in the outer shell and/or spiral scaffolds, and is included among the embodiments of the present invention. PLGA degrades completely in up to 6 weeks, depending on the ratio of lactic and glycolic acid in the polymer. While PCL completely degrades in up to 3 years, its mechanical properties start to degrade within 9 to 12 months. Although PCL is biocompatible and biodegradable, cells do not adhere easily to it because PCL does not provide cell recognition sites. Therefore by modifying the surface of the PCL layer with other substances, such as those discussed below, one can increase the ability of the polymer to have higher cellular attachment and proliferation. Further, the slow degradation rate of PCL is well-suited for cartilage regeneration, which may take up to one year or longer.

The use of PCL nanofibers in scaffolds made according to embodiments of the present invention maintains chondrocyte phenotype while allowing expression of cartilage-specific ECM genes. To support the nanofibers, a porous PCL sheet is used as a substrate for chondrocyte attachment, proliferation, and differentiation from mesenchymal stem cells. The porous PCL sheet is rolled into a spiral shape to form a three-dimensional scaffold, by which nanofibers deposited on the PCL sheet are arranged into a three-dimensional scaffold with high surface area and porosity. Due to the thinner walls of the spiral scaffold and the gaps therebetween, nutrient flow and metabolic waste removal can be greatly increased over other scaffolds in the prior art.

PLGA is also used in scaffolds made according to embodiments of the present invention to promote cell attachment. When sintered, PLGA microspheres provide scaffolds of the present invention with resistance to mechanical stresses, while allowing cell penetration and attachment through the pores in the sintered structure. By using the sintered microsphere structure, the surface area of the scaffold is increased, thus allowing increased cell proliferation and exposure of attached cells to apatite, chondroitin sulfate and hyaluronic acid.

Chondroitin sulfate (CS) is a sulfated GAG that covalently attaches to a core protein to form a proteoglycan, and is a natural component of the cartilage ECM. Such proteoglycans provide an increase in intracellular signaling, cell recognition, and interconnectivity. CS introduces bioactive and biosignaling sites to scaffolds of the present invention, causing chondrocytes to secret a greater amount of collagen. Since GAGs are the "filler" material between the cells, and there is a lower density of cells in the transitional and radial zones of cartilage, the GAG content should be higher in those zones. Thus, the lower areas of the scaffold will have a higher concentration of chondroitin sulfate and a lower concetrantion of hyaluronic acid. For the superficial layer, where the cellular density is higher, a lower concentration of GAGs should be present, and increasing amounts of collagen type II should be observed.

Hyaluronic acid (HA), a naturally occurring polysaccharide of alternating D-glucuronic acid and N-acetyl-D-glucosamine, functions as a core molecule for the binding of chondroitin sulfate when forming aggrecan (i.e., cartilage-specific proteoglycan core protein (CSPCP)). In studies involving equine models, it has been shown that HA has the potential to induce chondrogenesis from mesenchymal stem cells. Higher densities of HA should induce greater proliferation and attachment of cells to scaffolds of the present invention. HA has been shown to increase cellular DNA, chondrocyte metabolism, and greater collagen secretion.

Collagen type II is a main structural protein of articular cartilage to which proteoglycans can aggregate and provide compressive strength. It is biocompatible and has excellent cell-binding characteristics. Although collagen type II is readily degraded, the degradation period can be extended by combining the collagen type II with glycosaminoglycan and cross-linking.

Chitosan is a biodegradable cationic amino polysaccharide that can degrade into CS, dermatan sulfate, HA, keratin sulfate, and glycosylated collagen type II. Chitosan is hydrophilic, thus promoting cell adhesion, proliferation, and differentiation. Due to its structural similarity to glycosaminoglycan, it can increase chondrocyte attachment, proliferation, and biosynthetic activity when combined with other materials, such as hyaluronan. Chitosan's high positive charge allows for negatively-charged growth factors to be bound and delivered from the scaffold.

Dexamethasone is a glucocorticoid that acts as an anti-inflammatory and immunosuppressant agent. It has been shown to induce osteoblast differentiation and increase alkaline phosphatase activity, which is a marker of osteoblast differentiation. With the addition of dexamethasone, mineralization of tissue increases, leading to better formation of apatite. The addition of dexamethasone also prevents the growth of fibrous tissue due to vasoconstriction.

β-glycerophosphate has been shown to increase mineralization and induce formation of mineralized cartilage. The addition of factors such as β-glycerophosphate induces the chondrocytes to become mineralized cartilage. In the presence of β-glycerophosphate, chondrocytes form mineralized cartilage, but in the absence of β-glycerophosphate, there is little to no evidence of mineralization. Mineralized cartilage is an important layer in vertical integration of the scaffold as it helps transfer the load from the bone to the articular cartilage. Without this layer, cartilage is likely to fracture under compression.

Considering the materials discussed above, and referring back to osteochondral scaffold 10 of FIG. 1, a suitable material for the microspheres of the outer shell 12 would be PLGA/PCL with chitosan near the upper, cartilage-regenerative scaffold 14, and PGLA/PCL with chitosan and HA near the lower, bone-regenerative scaffold 16. Suitable size ranges for such microspheres would be 400-500 μm near the upper, cartilage-regenerative scaffold 14, and 300-400 μm near the lower, bone-regenerative scaffold 16. Suitable materials for electrospun nanofibers 28 on the outer surface 30 of the outer shell 12 would include PCL combined with ZVF (to increase lateral integration of regenerating cartilage tissue and reduce cellular apoptosis) in the vicinity of the upper, cartilage-regenerative spiral scaffold 14, and PCL combined with HA in the vicinity of the lower, bone-regenerative spiral scaffold 16 to increase integration of the regenerating bone tissue.

A suitable material for the upper, cartilage-regenerative scaffold 14 would be PCL with chitosan, in the form of a sheet, with electrospun nanofibers 20 arranged in orientations perpendicular to each other (e.g., horizontal and vertical relative to the length of the osteochondral scaffold 10). The electrospun nanofibers 20 may be formed and arranged such that there is a gradient of increasing collagen type II and decreasing CS and HA in a direction directed away from the separator layer 18.

A suitable material for the lower, bone-regenerative scaffold 16 would be PCL with chitosan and HA, in the form of a sheet, with electrospun nanofibers 22 of PCL with HA.

A suitable material for the separator layer 18 would be microspheres formed from PLGA/PLA with chitosan, β-glycerophosphate, and hydroxyapatite. A suitable size range for such microspheres would be 300-400 μm.

To deal with the cellular loss due to surgical debridement and scaffold insertion, electrospun nanofibers 28 may also be placed on the outside layer 30 of the outer shell 12 of the osteochondral scaffold 10. ZVF, a caspase inhibitor, has been shown to decrease apoptosis and the zone of death by reducing the percentage of cells that go through apoptosis due to the trauma of debridement. Thus, ZVF may be added to the nanofibers 2B spun onto the surface 30 of the outer shell 12 of the osteochondral scaffold 10. With the burst release of a caspase inhibitor, lateral integration of tissue should be increased due to the decreased distance between the acellular area and the zone of cellular death. When combined with the outside layer of electrospun nanofibers, ZVF increases lateral integration when compared to other scaffolds.

The use of multiple parallel aligned nanofibers can induce cells to align themselves to the nanofibers and secrete collagen type II and GAG in a similar fashion. Through the use of electrospun nanofibers, cells can attach and align themselves in a desirable orientation. With collagen fibril and proteoglycan secretion following the orientation of the cellular alignment, the ECM can be reconstructed, thus providing tissue that closely mimics natural cartilage, including hyaline cartilage. By electrospinning nanofibers in different orientations, while providing a directional chemical gradient, the different layers of articular cartilage can be differentiated by the collagen fiber alignment. Thus, by combining differently-aligned nanofibers to create a scaffold matching that of natural ECM, true articular cartilage can be formed.

Though nanofibers by themselves have the capability to regenerate one part of the ECM, another key factor is the reconstruction of the gradient of GAGs and collagen type II found in natural cartilage ECM. The unique mechanical properties of articular cartilage are in part due to the ultrastructure of articular cartilage with respect to this gradient. Without that gradient, the tissue eventually formed is unlikely to mimic the structure of natural articular cartilage. In natural articular cartilage, collagen type II ranges from 10-20% of the ECM, chondroitin sulfate 5-10% of the ECM, and hyaluronan 0.05-0.25% of the ECM. By varying the amount of these constituents, zones of regenerated articular cartilage can be differentiated to match the ultra-structure of natural articular cartilage. With the higher amount of proteoglycan in the lower parallel vertical nanofibers, the cellular density in that zone would be lower than in the zone of the parallel horizontally-aligned nanofibers. These GAGs are immobilized onto the microspheres and/or nanofibers via cross-linking.

The use of aligned nanofibers also provides an increase in the tensile strength of the regenerated cartilage, which is crucial for resisting shear and tensile forces from the articulating surfaces of the joints. The addition of nanofibers that are aligned parallel to the scaffold are able to increase the tensile strength of the scaffold, which will lead to an increase in tissue shear strength.

Expanding upon the foregoing discussion of FIGS. 1, 2A, 2B, 3A-3D, and 4, it is notable that osteochondral scaffolds made and used according to embodiments of the present invention resist the compressive mechanical stresses that will cause chondrocytes to go through apoptosis. Therefore, embodiments of the present invention can reduce or prevent compression of the tissue scaffold, which otherwise could cause cellular death and incomplete formation of bone or cartilage tissue. Additionally, the open top and bottom of the outer shell and spiral scaffolds allow cells to migrate from either the synovial fluid or from the bone marrow where stem cells originate. When compared to previously known scaffolds, where the top either is entirely composed of hydrogel or electrospun nanofibers, scaffolds made and used according to the present invention are more successful at providing the desirable physical properties of cartilage. When compared to grafts that use autologous chondrocytes, scaffolds made and used according to the present invention do not require harvested cells from a donor site, which would otherwise require additional surgery and additional costs.

To address concerns of mechanical strength, sintered polymeric microspheres are used to form 3D scaffolds. When such microspheres are used, the total glycosaminoglycan and overall histology of the newly formed tissue is greater and better than that achieved by autologous chondrocyte implantation. Previous studies show that microspheres made of PLGA and chitosan sintered together exhibited compressive moduli up to 412 MPa, much greater than the 0.5 to 0.7 MPa (dependent on a subject's age) for natural articular cartilage.

Figure 5A:
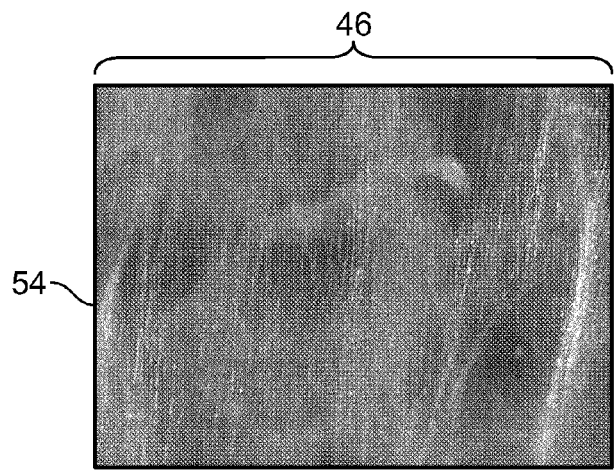
FIG. 5A is a photograph of a polymer sheet having vertically-oriented electrospun nanofibers thereupon, according to an embodiment of the present invention.
Figure 5B:
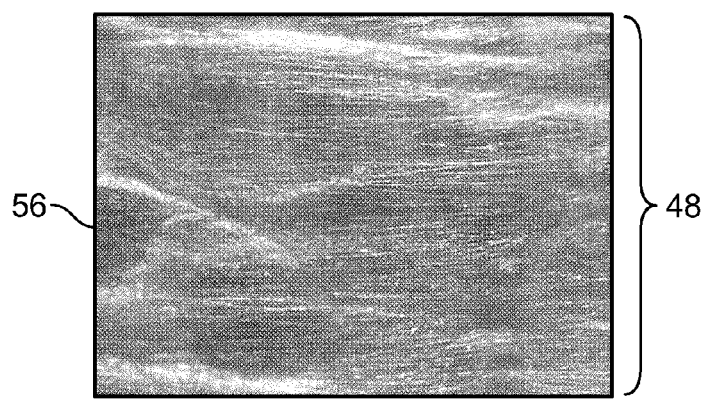
FIG. 5B is a photograph of a polymer sheet having horizontally-oriented electrospun nanofibers thereupon, according to an embodiment of the present invention.
Figure 5C:
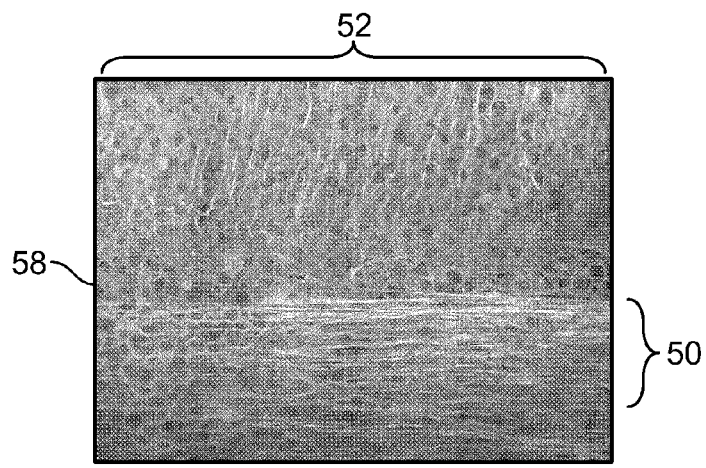
FIG. 5C is a photograph of a polymer sheet having both vertically-oriented and horizontally-oriented electrospun nanofibers thereupon, according to an embodiment of the present invention.

In addition to providing mechanical support, scaffolds made according to the present invention incorporate layers of different electrospun nanofibers to promote regeneration of the articular cartilage ECM. Because of the materials used, the dimensions of the graft can be varied accordingly to the defect size by varying the height, diameter, and depth of each layer. Aligned electrospun nanofibers having different orientations can be applied to the osteochondral scaffold to create an environment which mimics that of natural tissue. FIGS. 5A, 5B, and 5C are photographs of spiral scaffold materials having electrospun nanofibers 46, 48, 50, 52 on sheets 54, 56, 58 used to form spiral scaffolds. In FIG. 5A, the nanofibers 46 are oriented in a vertical direction relative to the length of the scaffold. In FIG. 5B, the nanofibers 48 are oriented in a horizontal direction relative to the length of the scaffold. FIG. 5C shows crossed layers of horizontally-oriented nanofibers 50 and vertically-oriented nanofibers 52. The horizontal and vertically-oriented nanofibers 50, 52 may be formed with different densities of nanofibers (e.g., number of nanofibers per millimeter), and different concentrations of various substances that stimulate cartilage or bone growth (e.g., CS, HA, or collagen type II).

Through the use of electrospun nanofibers, cells can attach to the scaffold and align themselves in orientations controlled by the orientations of the nanofibers. Nanofibers can also greatly increase the porosity of the scaffold while also increasing its surface area to allow for more cell attachment and better nutrient exchange with the extracellular fluids. With collagen fibrils and proteoglycan secretion following the orientation of the cellular alignment, the ECM can be reconstructed, thus providing a regenerated tissue that mimics natural tissue. To further enhance the utility of the electrospun nanofibers, scaffolds according to some embodiments of the present invention include nanofibers aligned in various orientations. By electrospinning aligned nanofibers so as to provide a directional gradient, the different layers of tissues can be differentiated by the resulting alignment of cell secretions. Thus, by combining differently aligned nanofibers to create a scaffold having a structure that simulates the natural ECM, regenerated cartilage having the zonal structure of native articular cartilage is allowed to form. A previous study involving osteochondral implants with bovine hide-derived collagen matrix nanofibers without zonal control arrangement, such as may be provided by the controlled orientation of nanofibers, showed no significant difference in collagen type II between the scaffold and control groups. The average collagen fiber diameter determined by transmission electron microscope studies for mature adults, is 34 nm, 70 to 100 nm, and 200 nm diameter for the superficial, median, and deep layers of the cartilage, respectively. Electrospun nanofibers having these diameters may be formed in a controlled fashion using conventional electrospinning techniques. Further, electrospinning is an attractive technique because it provides an opportunity to control morphology, porosity and composition of the scaffold using relatively unsophisticated equipment.

Fibers spun along the outside of the cartilage growth area on the osteochondral scaffold assist in lateral cell migration into the scaffold to the inner area of the osteochondral scaffold. By increasing lateral integration, the potential for fracturing can be minimized and it is more likely that the newly-formed cartilage can be fully integrated into the existing cartilage.

In some embodiments, the osteochondral scaffold disclosed herein is used in conjunction with autologous cell implantation, using cells from the patient. For faster tissue regeneration, the addition of autologous chondrocytes and osteoblasts harvested from the patient can be cultured onto the scaffold ex vivo before the scaffold is implanted into the defect. Cells could also be cultured ex vivo separately from the scaffold, harvested, then cultured onto the scaffold for a period of time before implantation.

Example

Fabrication and Testing of an Osteochondral Scaffold

The following is a non-limiting example of the fabrication and testing of an osteochondral scaffold according to an embodiment of the present invention. This example is merely meant to show how one type of osteochondral scaffold may be made. Both the osteochondral scaffold and the method of making it are included within the scope of the present invention.

Methods

Microsphere Formation

Microspheres of PLGA/PCL in proportions of 100/0, 75/25, or 50/50 were prepared by mixing 100% PLGA (85-15); 75% PLGA 25% PCL (MW: 80,000); or 50% PLGA 50% PCL as 10% (w/v) solutions in dichloromethylene (DCM) To create an water-in-oil emulsion effect, a 1% (w/v) poly(vinyl) alcohol (PVA) (MW: 31,000-50,000) solution was prepared and stirred at 360 RPM with an impeller. The polymer (i.e., PLGA or PLGA/PCL) solution was then loaded into a 10 ml syringe with a 16 gauge needle. The polymer solution was then forced out in a steady stream into the PVA solution. It was found that 300 ml of PVA solution could accept up to 25 ml of polymer solution. Once all of the polymer solution was injected into the PVA solution, the resulting emulsion was stirred continuously for 24 hours to allow the DCM to evaporate. The emulsion was then filtered with a triple wash using DI water to ensure that all of the PVA was washed away.

In procedures where hydroxyapatite is to be included in the microspheres, nanohydroxyapatite can be used instead of PCL in the procedure above, or can be coated onto the microspheres.

Once formed and dried, the microspheres were filtered into particle size ranges of 150 to 300 µm and 300 to 500 µm. The microspheres were then placed into a cylinder mold 8 mm in diameter by 11 mm in height with a metal dowel inserted therein to create a hollow cylinder of microspheres. Each microsphere blend was packed into the mold, then subjected to liquid sintering using a 50/50 or 90/10 blend of acetone/ethanol. The acetone/ethanol was allowed to evaporate, and the mold was placed into an oven at 70° C. for 4 hours to completely heat-sinter the microspheres.

Crosslinking of Chondroitin Sulfate and Hyaluronic Acid Microspheres

To crosslink the CS and HA sodium salt, these substances were first dissolved in DI water at 5% (w/v) and 0.5% (w/v), respectively. The microspheres were treated in 5% 1,6 hexanediamine (w/v) in isopropanol for 1 hour to aid in the subsequent cross-linking of the CS and HA, then rinsed once with DI water. The CS/HA solution was then injected into the scaffold and left to dry. To finish the crosslinking process, the scaffold was then treated with a carbodiimide solution (48 mM EDC and 6 mM NHS in 50 mM MES buffer at pH 5.5) for 24 hours at 37.5° C. The scaffold was then washed and lyophilized.

Mechanical Testing of Microsphere Scaffold

Ultimate yield compressive testing was carried out by inserting scaffolds into an Instron Tester using a 10 kN load cell and crushing the microsphere scaffold unconfined at a strain rate of 0.1 mm/minute. Cyclic testing was carried out by loading the scaffold into a confined aluminum well, wetting the scaffold with PBS, and subjecting the scaffold repeatedly to 50 N loads at 0.5 Hz for 10,200 cycles.

Preparation of PCL Sheet

PCL (MW: 70,000 to 90,000, Sigma, St. Louis, Mo.) was dissolved in DCM to form an 8% solution (w/v). To create a porous PCL sheet to be used as a nanofiber substrate, NaCl was ground to a diameter of 150-250 µm and coated onto a glass petri dish cover (Corning, Corning, N.Y.) with a 20% (w/v) glucose (Sigma, St. Louis, Mo.) solution. 6 ml of the 8% PCL solution was then poured into the glass petri dish, and allowed to dry for 4 minutes. Salt was then spread over the top of the PCL sheet and pressed down to create a porous network in the PCL sheet. Once completely dried, the salt was leached with DI water to release the PCL scaffold from the dish, leaving behind a porous structure as the salt dissolved. The sheets were then dried and cut into strips of 3 mm by 40 mm, with an average thickness of 0.35 mm per strip.

The spiral bone scaffold portion of the osteochondral scaffold was prepared by blending hydroxyapatite into the DCM solution while dissolving the PCL in ratios of 80/20 PCL/hydroxyapatite. The resulting solution was cast to form a PCL/hydroxyapatite sheet using the same casting method described above.

To crosslink CA and HA sodium salt, these substances were first dissolved to concentrations of 5% (w/v) and 0.5% (w/v) in DI water, respectively. The PCL sheet was then treated in 5% 1,6-hexanediamine (w/v) in isopropanol for 1 hour, then rinsed once with DI water. The CS/HA solution was then injected into the scaffold and left to dry. To finish the crosslinking process, the scaffold was then treated with a carbodiimide solution (48 mM EDC and 6 mM NHS in 50 mM MES buffer at pH 5.5) for 24 hours at 37.5° C. The scaffold was then washed and lyophilized. Similar techniques were used to crosslink HA, collagen type II, and/or CS onto microspheres.

Electrospinning of Nanofibers

Aligned nanofibers were laid down on scaffold materials at an electrical potential of 12 kV with a solution flow rate of 0.4 ml/hr. The distance from the needle tip to the substrate was 10 cm. Aligned nanofibers were spun for 2 minutes for a vertical orientation (i.e, along the direction intended to be parallel to the long axis of the finished osteochondral scaffold) and 10 minutes for a horizontal orientation (i.e, perpendicular to the vertical orientation). To provide different concentrations of CS and HA sodium salt for creating different CS/HA gradients in the top and bottom spiral scaffolds (i.e., 5% CS and 0.25% HA in the nanofibers of the top spiral scaffold, and 10% CS and 0.1% HA in the nanofibers of the bottom spiral scaffold), CS and HA were first dissolved in distilled water to form 30% working solutions each of CS and HA. The working solutions were added slowly to a 10% PCL solution in 1,1,1,3,3,3-hexafluoro-2-propanol (HFIP) (Oakwood Products, West Columbia, S.C.) (w/v) until the desired CS and HA percentages were obtained.

To create a layer of aligned nanofibers, two steel blocks were placed with the PCL sheet laid across the blocks. Upon electrospinning of the PCL solutions, the nanofibers were directed across the PCL sheet in a parallel fashion. A piece of paper was used to block one side of the PCL sheet from being covered with nanofibers. The perpendicular orientation of a second layer of nanofibers, laid over the first layer, was achieved by turning the PCL sheet 90 degrees from its initial orientation, then laying down the second layer of nanofibers using the same procedure used to lay down the first layer. Once the electrospun nanofibers had been laid onto PCL sheets, the PCL sheets were curled into spiral shapes using tweezers. The spiral sheets were then wrapped with copper strips to hold the spiral shape, and heat-formed at 50° C. for 50 minutes to form the spiral scaffolds.

Crosslinking HA and CS

The spiral scaffolds formed as described above were then submersed in the hexanediamine solution to treat the nanofibers so that HA and CS in the nanofibers could be crosslinked. To finish the crosslinking process, the spiral scaffolds were then treated with a carbodiimide solution (48 mM EDC and 6 mM NHS in 50 mM MES buffer at pH 5.5) for 24 hours at 37.5° C. The spiral scaffolds were then washed and lyophilized.

Assembly of the Osteochondral Scaffold

The complete osteochondral scaffold was assembled by inserting the osteogenic (bone-inducing) and chondrogenic (cartilage-inducing) scaffolds into their corresponding locations in the sintered-microsphere shell, the thinner-walled end of the shell accommodating the chondrogenic spiral scaffold with dual fiber alignment, and the thicker-walled end of the shell accommodating the osteogenic spiral scaffold (refer to FIG. 1 and its related discussion above).

Results

Figure 6A:
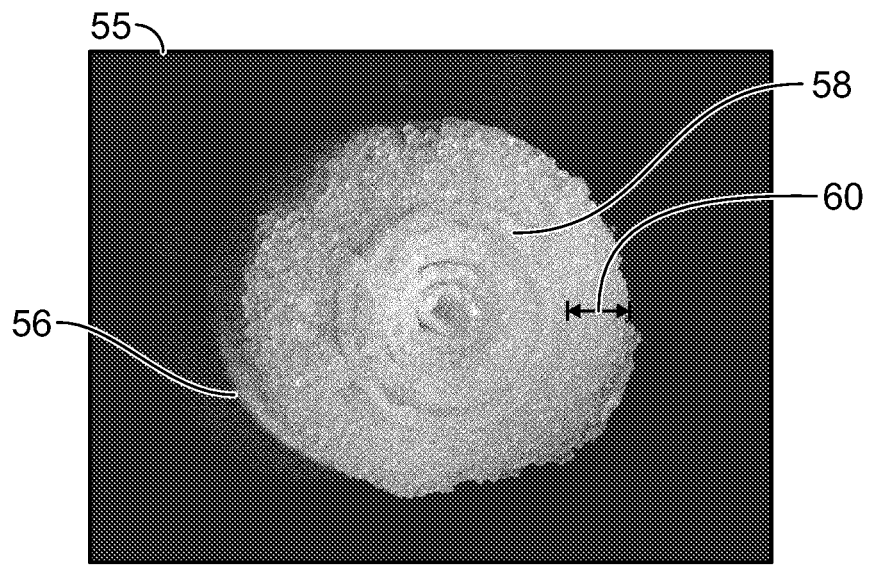
FIG. 6A is an optical microscopy image of the top view of an osteochondral scaffold prepared according to an embodiment of the present invention.
Figure 6B:
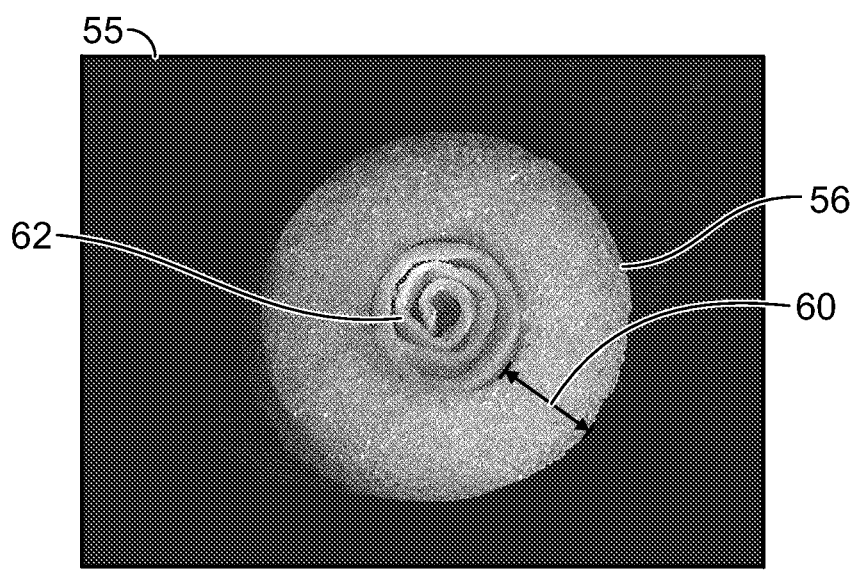
FIG. 6B is an optical microscopy image of the bottom-view of an osteochondral scaffold prepared according to an embodiment of the present invention.

FIGS. 6A and 6B are optical microscopy images of an osteochondral scaffold 55 according to an embodiment of the present invention as prepared by the method described above.

FIG. 6A is an image of the top view (i.e., cartilage-forming end) of the osteochondral scaffold 55 showing its outer shell 56 and chondrogenic spiral scaffold 58. In such an embodiment, the outer shell 56 may be made of microspheres of 100% PLGA or with varying ratios of PLGA/PCL. In the embodiment shown, the wall 60 of the outer shell 56 is about 1 mm thick. The chondrogenic scaffold 58 of the embodiment shown consists of a porous PCL sheet with vertically-aligned and horizontally-aligned PCL nanofibers (not shown) with gradients of CA and HA. Layered nanofibers wherein one layer is vertically-aligned and another is horizontally-aligned are also referred to herein as "dually-aligned."

FIG. 6B is an image of the bottom view (i.e., bone-forming end) of the osteochondral scaffold 55 of FIG. 6A showing the outer shell 56 and osteogenic spiral scaffold 62. In the embodiment shown, the wall 60 of the outer shell 56 is about 2 mm thick, to provide additional compressive strength at the bone-forming end of the scaffold relative to the cartilage-forming end shown in FIG. 6A. The osteogenic spiral scaffold 62 consists of a porous PCL sheet with randomly-oriented nanofibers (not shown). In other embodiments of the present invention, the materials for the spiral scaffold 62 and nanofibers can have various ratios of PCL and a ceramic material, such as hydroxyapatite or beta-tricalcium phosphate.

Figure 7:
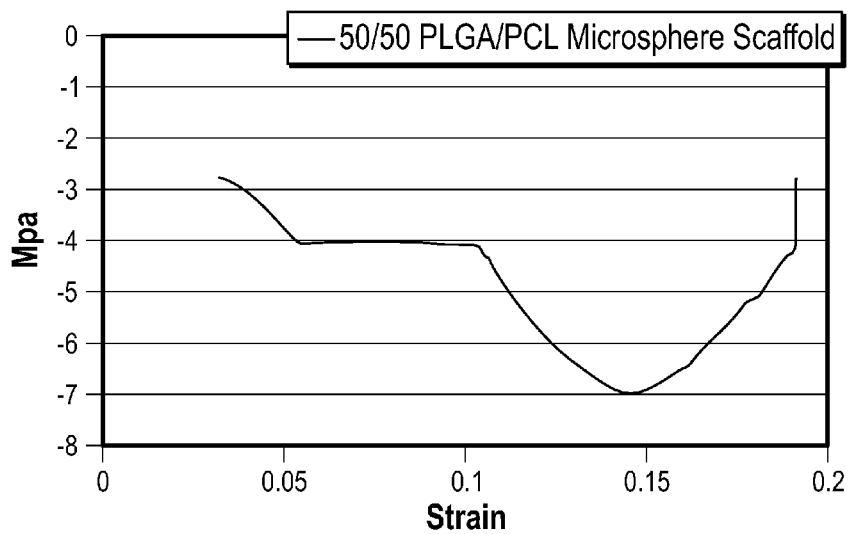
FIG. 7 is a plot showing stress versus strain of one compression test till failure of the outer shell for an osteochondral scaffold prepared according to an embodiment of the present invention.
Figure 8:
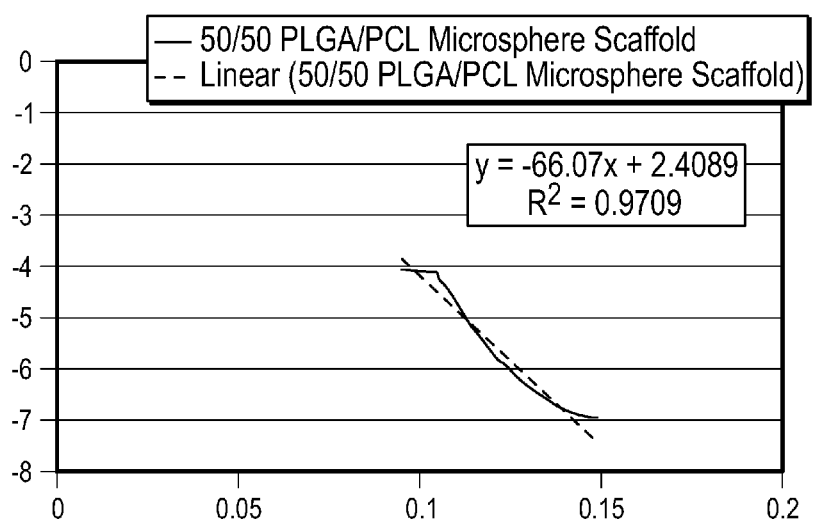
FIG. 8 is a plot showing the elastic modulus of the outer shell for an osteochondral scaffold prepared according to an embodiment of the present invention.
Figure 9:
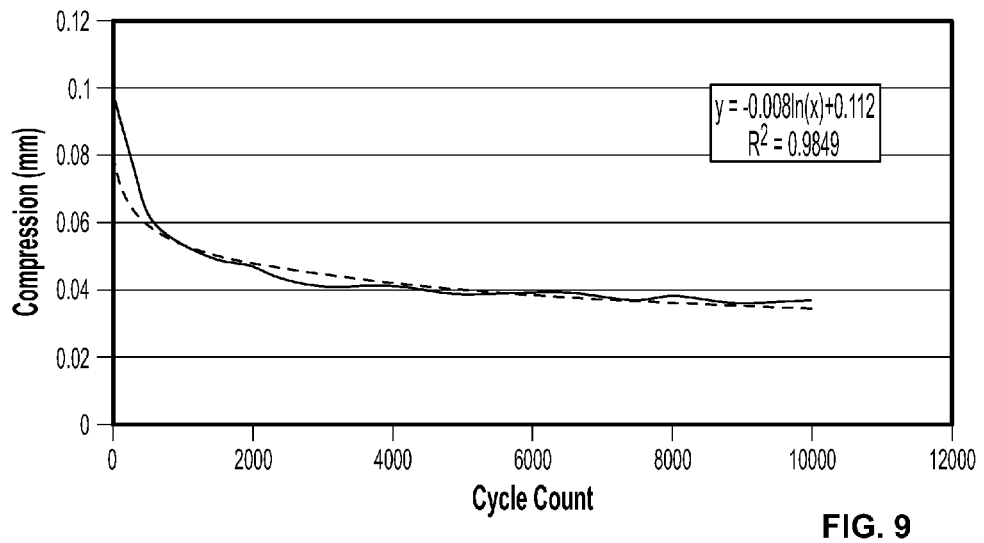
FIG. 9 is a plot of the cyclic compression testing of an outer shell for an osteochondral scaffold prepared according to an embodiment of the present invention.

FIGS. 7, 8 and 9 are plots illustrating the results of compressive testing of PLGA/PCL sintered-microsphere outer shells for an osteochondral scaffold. Preparation of the outer shells, and the testing methodology are described above in the Methods section.

FIG. 7 is a plot showing stress versus strain of one compression test till failure of a 50/50 PLGA/PCL blend microsphere scaffold, showing an average ultimate compressive yield strength of 6.276+/−0.44 MPa of stress. FIG. 8 is a plot showing the elastic modulus of the outer shell, based on the test of FIG. 7, showing an elastic modulus of 66.07+/−5.61 MPa. FIG. 9 is a plot of the cyclic testing of a 75/25 PLGA/PCL microsphere outer shell scaffold for 10,000 cycles at 50 N compression at a rate of 0.5 Hz. Given the area of the scaffold, the load translates to 1.6 MPa. The log curve fit shows that as the cycles increase the compression will become smaller and the likelihood of structural failure decreases.

FIGS. 7-9 thus show that the compressive mechanical properties of the 50/50 PLGA/PCL scaffold were able to withstand the normal stresses to which cartilage are subjected in the human body. The ultimate compressive yield strength of 6.276+/−0.44 MPa exceeded the strengths of 1 to 5 MPa typical for osteochondral plugs known in the art. The compressive strength of the outer shell tested definitely exceeded the ultimate yield strengths of 0.5 to 0.7 MPa of normal human articular cartilage. The elastic modulus obtained was 66.07+/−5.61 MPa which exceeds the range of 1.36 to 39.2 MPa of normal human articular cartilage. The cyclic loading of the 75/25 PLGA/PCL outer shell showed that even at 10,000 compressive cycles, the outer shell could resist the normal stresses of repetitive loads of up to 1 MPa, such as are generated by walking. As can be seen from FIG. 9, an asymptote can be seen, indicating that the outer shell had settled to its ultimate dimensions. If there had been an issue with deformation of the outer shell, the amount of compression would have continued to increase as the number of compressive cycles increased.

Figure 10:
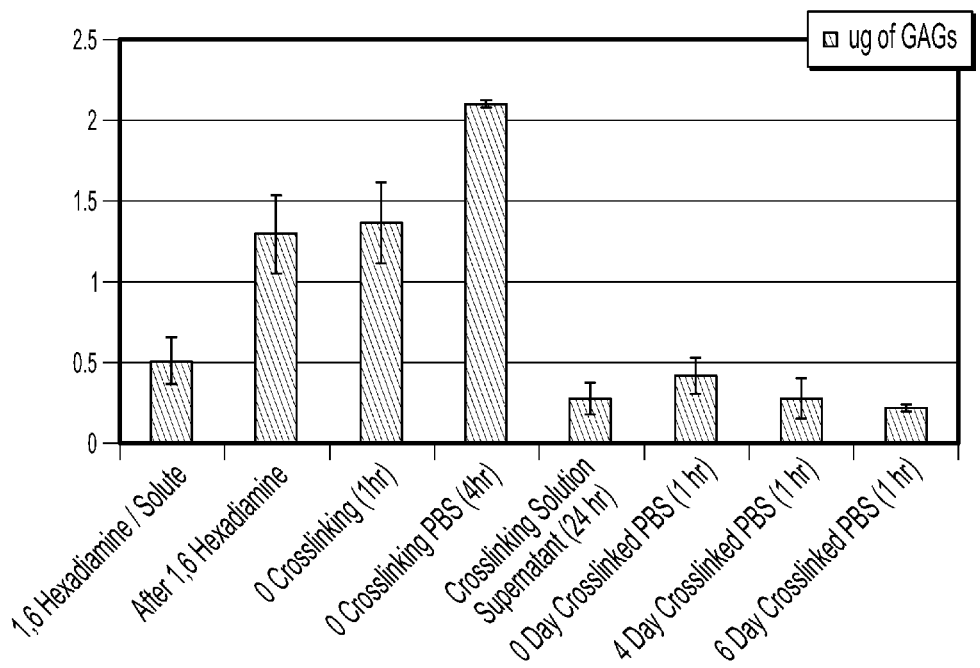
FIG. 10 is a bar graph illustrating the increased retention of GAGs on a PCL sheet having dually-aligned nanofibers as the degree of cross-linking of the GAGs increases, according to an embodiment of the present invention.

FIG. 10 is a bar graph illustrating the increased retention of GAGs (i.e., CS and HA) on a PCL sheet having dually-aligned nanofibers as the degree of cross-linking increases. In the PCL sheets tested, the horizontally aligned nanofibers were made of PCL with 5% chondroitin sulfate and 0.25% hyaluronic acid, while the vertically aligned nanofibers are made of PCL with 10% chondroitin sulfate and 0.1% hyaluronic acid. FIG. 10 tracks the amount of GAGs leached into a PBS supernatant during the crosslinking process. It can be seen that GAGs are present before the crosslinking process is complete. It can also be seen, after cross-linking, there is a significant decrease in elution of GAGs into the supernatant, indicating successful crosslinking and immobilization of CS and HA. It was also observed that, before crosslinking, staining with alcian blue showed that GAGs were leached out of the PCL/nanofibers system (i.e., no staining was observed). After cross-linking, alcian blue stain was observed across the entire area where nanofibers had been laid, indicating that GAGs had been retained in the nanofibers. These tests showed that cold water washings the nanofibers did not wash away the GAGs after crosslinking was completed.

Figure 11:
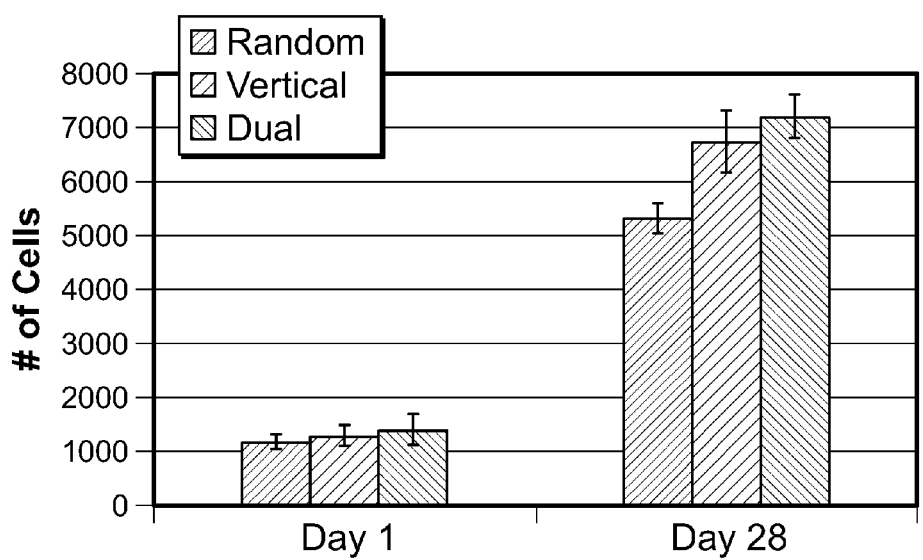
FIG. 11 is a bar graph of the attachment and proliferation of human chondrocytes on scaffolds of the present invention having different alignments of nanofibers.

FIG. 11 is a bar graph of the attachment and proliferation of human chondrocytes on scaffolds having different alignments of nanofibers at days 1 and 28 after the scaffolds were seeded. The DNA assay of the differently aligned scaffolds show that while attachment of human chondrocytes at day 1 was similar for randomly, vertically, and dually-aligned scaffolds, there was a significant difference in proliferation at day 28 with both vertically and dually-aligned nanofibers having a greater effect on the proliferation of chondrocytes. The symbol "*" indicates the presence of significantly different amounts of chondrocytes when compared to the randomly oriented group ($p<0.5$). These results indicate that the presence of aligned nanofibers do indeed have an impact on the proliferation of chondrocytes. This, in turn, promotes shorter healing times and formation of tissue that more closely resembles natural cartilage.

Figure 12:
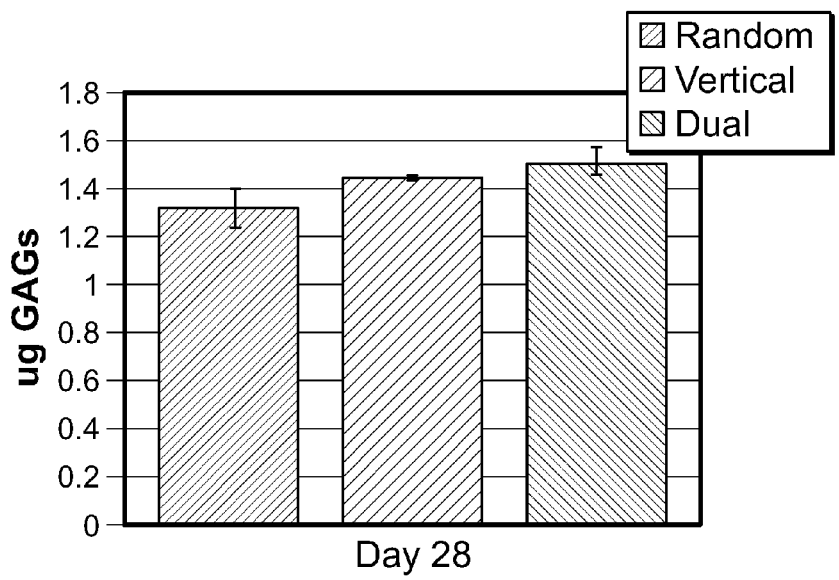
FIG. 12 is a bar chart showing GAG assays performed on scaffolds of the present invention having different alignments of nanofibers.

FIG. 12 is a bar chart showing GAG assays performed by dimethylmethlyene blue (DMMB) staining for scaffolds having different alignments of nanofibers. The GAG assays show that GAG secretion for vertically and dually-aligned scaffolds at day 14 were significantly different than the GAG secretion for scaffolds having randomly oriented nanofibers. The symbol "*" indicate significant differences in GAG secretion compared to the randomly oriented group ($p<0.5$). Increased amounts of GAG lead to increased proteoglycan formation, which in turns leads to stronger tissue with better compressive stress resistance.

Figure 13:
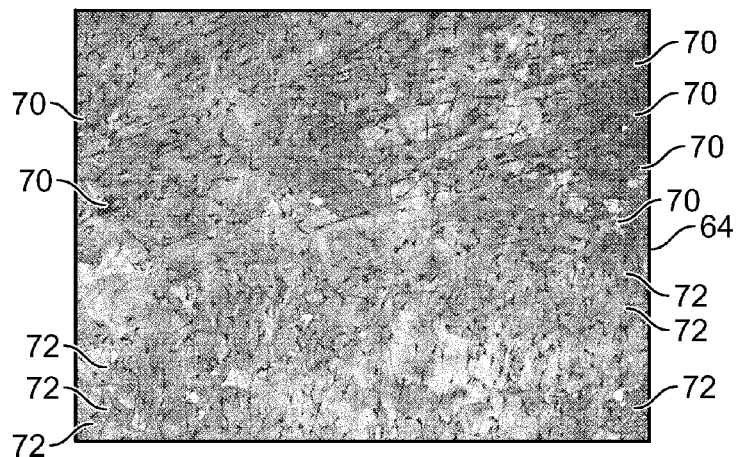
FIG. 13 is an optical microscopy image showing the alignment of chondrocytes on polymer sheets having both horizontally-oriented and vertically-oriented nanofibers, according to an embodiment of the present invention.
Figure 14:
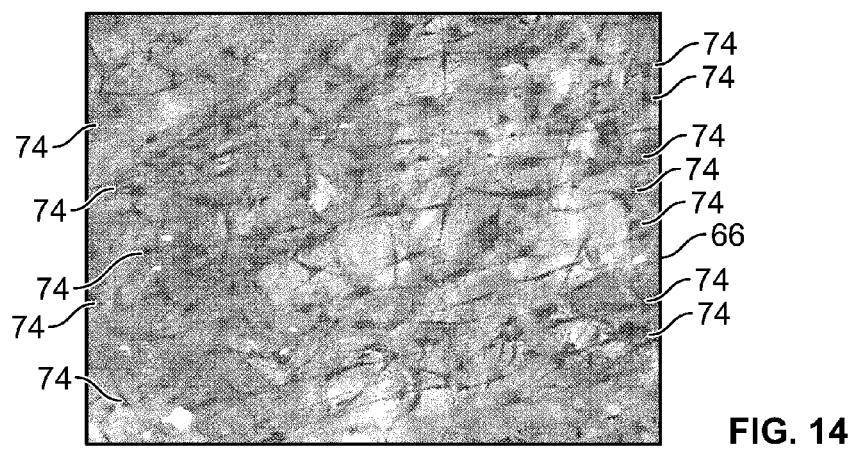
FIG. 14 is an optical microscopy image showing the alignment of chondrocytes on polymer sheets having horizontally-oriented nanofibers, according to an embodiment of the present invention.
Figure 15:
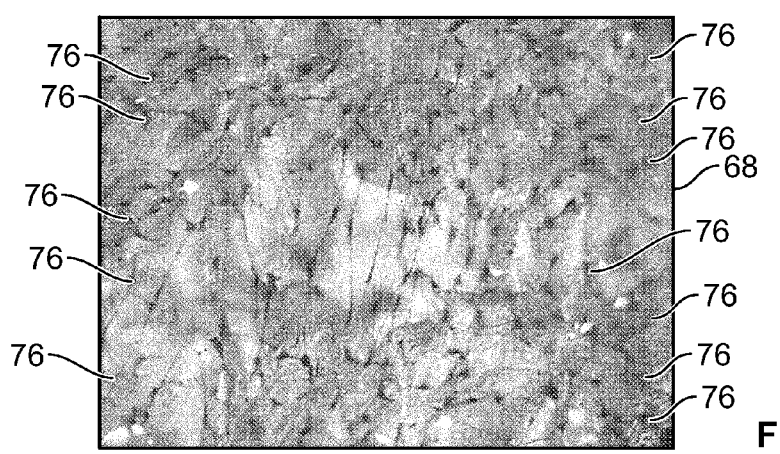
FIG. 15 is an optical microscopy image showing the alignment of chondrocytes on polymer sheets having vertically-oriented nanofibers, according to an embodiment of the present invention.

FIGS. 13-15 are optical microscopy images of methylene blue DNA staining of chondrocytes seeded, respectively, on dually-aligned, horizontally-aligned, and vertically-aligned PCL nanofibers 64, 66, 68 at day 14. The dark objects 70, 72, 74, 76 indicate the presence of cellular matrix (i.e., proliferating chondrocytes). Taken together, FIGS. 13-15 show the visual alignment of the cells through DNA staining by methylene blue, confirming that the aligned nanofibers induce an alignment of the cell matrix induced by the aligned nanofibers.

It will be understood that the embodiments of the present invention that are described herein is merely exemplary and that a person skilled in the art may make many variations and modifications without departing from the spirit and scope of the invention. All such variations and modifications are intended to be included within the scope of the invention as described in the attached claims.

We claim:

1. An osteochondral scaffold, comprising:
   a cylindrical outer shell having a longitudinal axis and including a plurality of microspheres sintered together as a unitary structure having a first hollow end and a second hollow end opposite said first hollow end;
   a first polymeric sheet having a first plurality of first nanofibers substantially aligned with each other thereupon, said first polymeric sheet having the shape of a first spiral with first coils and having first gaps between adjacent ones of the first coils, said first polymeric sheet residing in said first hollow end of said outer shell;
   a second polymeric sheet having a second plurality of second nanofibers substantially aligned with each other thereupon, said second polymeric sheet having the shape of a second spiral with second coils and second gaps between adjacent ones of the second coils, said second polymeric sheet residing in said second hollow end of said outer shell, wherein said microspheres, said first nanofibers, and said second nanofibers have cell recognition sites, said first nanofibers having first compositions that include at least one glycosaminoglycan that provides first cell recognition sites on the first nanofibers, said second nanofibers having second compositions that include at least one osteogenic substance that provides second cell recognition sites on the second nanofibers, said first composition promoting attachment and proliferation of chondrocytes on said first nanofibers, said second composition promoting attachment and proliferation of osteoblast precursor cells on said second nanofibers, and said first composition being different from said second composition.

2. The osteochondral scaffold of claim 1, wherein said at least one glycosaminoglycan is selected from the group consisting of hyaluronic acid and chondroitin sulfate.

3. The osteochondral scaffold of claim 1, wherein said first and second nanofibers include polycaprolactone and said microspheres include poly (lactic glycolic) acid.

4. The osteochondral scaffold of claim 1, wherein at least some of said microspheres are proximate said first hollow end of said outer shell and include a third composition promoting attachment and infiltration of mesenchymal stem cells through said outer shell, and at least some of said microspheres are proximate said second hollow end of said outer shell and include a fourth composition promoting attachment and infiltration of mesenchymal stem cells among the microspheres.

5. The osteochondral scaffold of claim 1, wherein said first polymeric sheet has a third plurality of third nanofibers on said first plurality of first nanofibers, said third plurality of third nanofibers being substantially aligned with each other in a direction that is substantially perpendicular to said first plurality of first nanofibers.

6. The osteochondral scaffold of claim 5, wherein said third nanofibers have third compositions that include a third at least one glycosaminoglycan that provides third cell recognition sites on the third nanofibers, said third composition being different from said second composition and promoting attachment, proliferation, and differentiation of mesenchymal stem cells into chondrocytes on said third nanofibers.

7. A method of making an osteochondral scaffold, comprising the steps of:
preparing an outer shell having a longitudinal axis and including a plurality of microspheres sintered together as a unitary mass, the microspheres including a polymer that promotes attachment and infiltration of osteoblast precursor cells among the microspheres, the outer shell having a first hollow end and a second hollow end opposite the first hollow end;
preparing a first polymeric sheet having a first surface;
laying a first plurality of first nanofibers on the first surface of the first polymeric sheet, the first plurality of first nanofibers being substantially aligned with one another, the first nanofibers having a first composition including at least one glycosaminoglycan that provides first cell recognition sites on the first nanofibers, the first composition promoting attachment, proliferation, and differentiation of mesenchymal stem cells into chondrocytes on the first nanofibers;
chemically cross-linking the first at least one glycosaminoglycan so as to immobilize the first at least one glycosaminoglycan on the first nanofibers;
curling the first polymeric sheet to have the shape of a first spiral with first gaps between adjacent ones of the first coils;
heat-treating the curled first polymeric sheet such that it retains the shape of the first spiral;
placing the curled first polymeric sheet into the first hollow end of the outer shell;
preparing a second polymeric sheet having a second surface;
laying a second plurality of second nanofibers on the second surface of the second polymeric sheet, the second plurality of second nanofibers being substantially aligned with one another, the second nanofibers having a second composition including at least one osteogenic substance that provides second cell recognition sites on the second nanofibers, the second composition promoting attachment and proliferation of osteoblast precursor cells on the second nanofibers, the second composition being different from the first composition;
chemically cross-linking the second at least one glycosaminoglycan so as to immobilize the second at least one glycosaminoglycan on the second nanofibers;
curling the second polymeric sheet to have the shape of a second spiral with second gaps between adjacent ones of the second coils;
heat-treating the curled second polymeric sheet such that it retains the shape of the second spiral; and
placing the curled second polymeric sheet into the second hollow end of the outer shell.

* * * * *